United States Patent
Rea et al.

(10) Patent No.: US 10,370,675 B2
(45) Date of Patent: Aug. 6, 2019

(54) TRANSGENIC PLANTS EXHIBITING ENHANCED PHYTOCHELATIN-BASED HEAVY METAL TOLERANCE AND METHODS OF USE THEREOF

(71) Applicants: The Trustees of the University of Pennsylvania, Philadelphia, PA (US); Washington University in St. Louis, St. Louis, MO (US); Donald Danforth Plant Science Center, St. Louis, MO (US)

(72) Inventors: Philip A. Rea, Ardmore, PA (US); Joseph Jez, Kirkwood, MO (US); Rebecca Cahoon, Lincoln, NE (US)

(*) Notice: Subject to any disclaimer, the term of this patent is extended or adjusted under 35 U.S.C. 154(b) by 0 days.

(21) Appl. No.: 15/602,757

(22) Filed: May 23, 2017

(65) Prior Publication Data

US 2017/0342436 A1 Nov. 30, 2017

Related U.S. Application Data

(60) Provisional application No. 62/340,931, filed on May 24, 2016.

(51) Int. Cl.
| | | |
|---|---|---|
| C12N 15/82 | (2006.01) | |
| C12N 9/10 | (2006.01) | |
| C02F 3/32 | (2006.01) | |
| C02F 101/20 | (2006.01) | |
| C02F 103/06 | (2006.01) | |

(52) U.S. Cl.
CPC ............ *C12N 15/8271* (2013.01); *C02F 3/32* (2013.01); *C12N 9/104* (2013.01); *C12Y 203/02015* (2013.01); *C02F 2101/20* (2013.01); *C02F 2103/06* (2013.01)

(58) Field of Classification Search
None
See application file for complete search history.

(56) References Cited

U.S. PATENT DOCUMENTS 6,489,537 B1* 12/2002 Rea ........................ C12N 9/104
435/320.1

OTHER PUBLICATIONS

Cahoon et al, The Journal of Biological Chemistry, Jul. 10, 2015, vol. 290, No. 28, pp. 17321-17330 (Year: 2015).*
Vatamaniuk et al, The Journal of Biological Chemistry, 2004, vol. 279, No. 21, pp. 22449-22460. (Year: 2004).*
Bick, Julie-Ann et al., "Regulation of the Plant-type 5'-Adenylyl Sulfate Reductase by Oxidative Stress", Biochemistry, 40: 9040-9048 (2001).
Cameron, Jeffrey C. et al., "Essential Role of Glutathione in Acclimation to Environmental and Redox Perturbations in the Cyanobacterium *synechocystis* sp. PCC 6803", Plant Physiology, 154: 1672-1685 (2010).
Chias, J.C. et al., Tentative identification of the second substrate binding site in *Arabidopsis phytochelatin* synthase, PLoS One, 8: e82675 (2013).
Clemens, S. et al., "Plant science: the key to preventing slow cadmium poisoning", Trends Plant Sci., 18: 92-99 (2013).
Corbett, C. et al., Phytochelatins and metallothioneins: roles in heavy metal detoxification and homeostasis, Annu. Rev. Plant Biol., 53: 159-182 (2002).
Gasic, K. et al. Transgenic Indian musgtard (*Brassica juncea*) plants expressing an *Arabidopsis* phytochelatin synthase (AtPCS1) exhibit enhanced As and Cd Tolerance, Plant Mol. Biol., 64: 361-369 (2007).
Gasic K. et al., Expression of *Arabidopsis* phytochelatin synthease in Indian mustard (*Brassica juncea*) plants enhances tolerance for Cd and Zn, Planta, 225: 1277-1285 (2007).
Griffith, O.W., "Determination of glutathione and glutathione disulfide using glutathione reductase and 2-vinylpyridine", Anal. Biochem., 106: 207-212 (1980).
Gromes, R. et al., "The redox switch of gamma-glutamylcysteine ligase via a reversible monomer-dimer transition is a mechanism unique to plants", Plant J., 54: 1063-1075 (2008).
Hicks, L.M. et al., "Thiol-based regulation of redox-active glutamate-cysteine ligase from *Arabidopsis thaliana*", lant Cell, 19: 2653-2661 (2007).
Hothorn, M. et al., "Structural basis for the redox control of plant glutamate cysteine ligase", J. Biol. Chem., 281: 27557-27665 (2006).
Howden, R. et al., "Cadmium-sensitive, cad1 mutants of *Arabidopsis thaliana* are phytochelatin deficient", Plant Physiol, 107: 1059-1066 (1995).
Howden, R. et al., "A cadmium-sensitive, glutathione-deficient mutant of *Arabidopsis thaliana*", Plant Physiol, 107: 1067-1073 (1995).
Jez, J.M. et al., *Arabidopsis thaliana* glutamate-cysteine ligase: functional properties, kinetic mechanism, and regulation of activity, J. Biol. Chem. 279: 33463-33470 (2004).
Jez, J.M. et al., "Kinetic mechanism of glutathione synthetase from *Arabidopsis thaliana*", J. Biol. Chem., 279: 42726-42731 (2004).
Johnson, M.D. et al., "Cadmium mimics the in vivo effects of estrogen in the uterus and mammary gland", Nature Med. 9: 1081-1084 (2003).
Lassner, M. et al., "Directed molecular evolution in plant improvement", Curr. Opin. Plant Biol., 4: 152-156 (2001).
Lee, S. et al., "Overexpression of *Arabidopsis* phytochelatin synthase paradoxically leads to hypersensitivity to cadmium stress", Plant Physiol, 131: 656-663 (2003).
Li, Y. et al., "A new pathway for vacuolar cadmium sequestration in *Saccharomyces cerevisiae*: YCF1-catalyzed transport of bis(glutathionato)cadmium", Proc. Natl. Acad. Sci. USA, 94: 42-47 (1997).

(Continued)

*Primary Examiner* — Eileen B O Hara
(74) *Attorney, Agent, or Firm* — Kathleen D. Rigaut; Howson & Howson LLP

(57) ABSTRACT

Transgenic plants exhibiting phytochelatin-based heavy metal tolerance and methods of use thereof for bioremediation are disclosed.

15 Claims, 8 Drawing Sheets
(7 of 8 Drawing Sheet(s) Filed in Color)

Specification includes a Sequence Listing.

(56) References Cited

OTHER PUBLICATIONS

Li, Y. et al., "Overexpression of Phytochelatin Synthase in *Arabidopsis* Leads to Enhanced Arsenic Tolerance and Cadmium Hypersensitivity".

Loeffler, S. et al., "TErmination of the phytochelatin synthase reaction through sequestration of heavy metals by the reaction product", FEBS Lett., 258: 42-46 (1989).

Lu, Y.P. et al., "AtMRP1 gene of *Arabidopsis* encodes a glutathione S-conjugate pump: isolation and functional definition of a plant ATP-binding cassette transporter gene", Proc. Natl. Acad. Sci. USA, 94: 8243-8248 (1997).

Meister, A. et al., "Glutathione biosynthesis and its inhibition", Methods Enzymol., 252: 26-30 (1995).

Mendoza-Cozatl, D.G. et al., Tonoplast-localized Abc2 transporter mediates phytochelatin accumulation in vacuoles and confers cadmium tolerance, J. Biol. Chem., 285: 40416-40426 (2010).

Park, J. et al., "The phytochelatin transporters AtABCC1 and AtABCC2 mediate tolerance to cadmium and mercury", Plant J., 69: 278-288 (2012).

Pilon-Smits, EAH et al., "Phytoremedition of metals using transgenic plants", Crit. Rev. Plant Sci., 21: 439-456 (2002).

Pomponi, M. et al., "Overexpression of *Arabidopsis* phytochelatin synthase in tobacco plants enhances Cd(2+) tolersance and accumulation but not translocation to the shoot", Plants, 223: 180-190 (2006).

Rea, P.A., "Phytochelatin synthase: of a protease a peptide polymerase made", Physiol. Plant., 145: 154-164 (2012).

Rea, P.A. et al., "Weeds, worms, and more: papain's long-lost cousin, phytochelatin synthase", Plant Physiol., 136: 2463-2474 (2004).

Romanyuk, N.D. et al., "Mutagenic definition of a papain-like catalytic triad, sufficiency of the N-terminal domain for single-site core catalytic enzyme acylation, and C-terminal domain for augmentative metal activation of a eukaryotic phytochelatin synthase", Plant Physiol, 141: 858-869 (2006).

Rugh, C.L. et al., "Mercuric ion reduction and resistance in transgenic *Arabidopsis thaliana* plants expressing a modified bacterial merA gene", Proc. Natl. Acad. Sci. USA, 93: 3182-3187 (1996).

Ruotolo, R. et al., Domain organization of phytochelatin synthase: functional properties of truncated enzyme species identified by limited proteolysis, J. Biol. Chem., 279: 14686-14693 (2004).

Salt, D.E. et al., "Phytoremediation", Annu. Rev. Plant Physiol. Plant Mol. Biol., 49: 643-668 (1998).

Song, W.Y. et al., "Engineering tolerance and accumulation of lead and cadmium in transgenic plants", Nature Biotech., 21: 914-919 (2003).

Song, W. Y. et al., Arsenic tolerance in *Arabidopsis* is mediated by two ABCC-type phytochelatin transporters, Proc. Natl. Acad,. Sci. USA, 107: 21187-21192 (2010).

Vatamaniuk, O.K. et al., "AtPCS1, a phytochelatin synthase from *Arabidopsis*: isolation and in vitro reconstruction", Proc. Natl. Acad. Sci. USA, 96: 7110-7115 (1999).

Vatamaniuk, O.K. et al., "Mechanism of heavy metal ion activation of phytochelatin (PC) synthase: blocked thiols are sufficient for PC synthase-catalyzed transpeptidation of glutathione and related thiol peptides", J. Biol. Chenm., 275: 31451-31459 (2000).

Vatamaniuk, O.K. et al., A new pathway for heavy metal detoxification in animals: phytochelatin synthase is required for cadmium tolerance in Caenorhabditis elegans., J. Biol. Chem., 276: 20817-20820 (2001).

Vatamaniuk, O.K. et al., "Phytochelatin synthase, a dipeptidyltransferase that undergoes multisite acylation with gamma-glutamylcysteine during catalysis: stoichiometric and site-directed mutagenic analysis of *Arabidopsis thaliana* PCS1-catalyzed phytochelatin synthesis", J. Biol. Chenm., 279: 22449-22460 (2004).

Vivares, D. et al., A papain-like enzyme at work: native and acyl-enzyme intermediate structures in phytochelatin synthesis, Proc. Natl. Acad. Sci. USA, 102: 18848-18853 (2005).

Winterbourn, C.C., "Reconciling the chemistry and biology of reactive oxygen species", Nature Chem. Biol., 4: 278-286 (2008).

Zhu, Y. et al., "Overexpression of glutathione synthease in indian mustard enhances cadmium accumulation and tolerance", Plant Physiol., 119: 73-80 (1999).

Zhu, Y.L. et al., "Cadmium tolerance and accumulation in Indian mustard is enhanced by overexpressing gamma-glutamylcysteine synthetase", Plant Physiol., 121: 1169-1178 (1999).

Dhankher, Om et al., "Engineering tolerance and hyperaccumulation of arsenic in plants by combining arsenate reductase and gamma-glutamylcysteine synthetase expression", Nature Biotech., 20: 1140-1145 (2002).

Ha, S-B. et al., "Phytochelatin Synthase Genes from *Arabidopsis* and the Yeast *Schizosaccharomyces pombe*", The Plant Cell, 11: 1153-1163 (1999).

* cited by examiner

Fig. 8

SEQUENCE LISTING

<160> NUMBER OF SEQ ID NOS: 18

<210> SEQ ID NO 1
<211> LENGTH: 485
<212> TYPE: PRT
<213> ORGANISM: Arabidopsis thaliana

<400> SEQUENCE: 1

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Ala Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Val Lys Cys Thr Ser Ser Glu Asn Cys
    130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

```
Gly Pro Asp Asp Ser Glu Gly Thr Val Val Thr Gly Val Val Arg
    370             375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
            435                 440                 445

Ser Leu Pro Thr Leu Leu Gln Glu Val Leu His Leu Arg Arg Gln
450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 2
<211> LENGTH: 485
<212> TYPE: PRT
<213> ORGANISM: Artificial Sequence
<220> FEATURE:
<223> OTHER INFORMATION: V97L

<400> SEQUENCE: 2

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
            35                  40                  45

Thr Gln Ser Glu Pro Ala Tyr Cys Gly Leu Ala Ser Leu Ser Val Val
        50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Leu Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
            115                 120                 125

Asp Asp Phe Arg Lys Phe Val Val Lys Cys Thr Ser Ser Glu Asn Cys
130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
            195                 200                 205

Lys Arg Arg Gly Phe Met Leu Ile Ser Arg Pro His Arg Glu Pro Gly
        210                 215                 220

Leu Leu Tyr Thr Leu Ser Cys Lys Asp Glu Ser Trp Ile Glu Ile Ala
225                 230                 235                 240
```

Lys Tyr Leu Lys Glu Asp Val Pro Arg Leu Val Ser Gln His Val
            245                 250                 255

Asp Ser Val Glu Lys Ile Ile Ser Val Val Phe Lys Ser Leu Pro Ser
        260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
            325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
            355                 360                 365

Gly Pro Asp Asp Ser Glu Gly Thr Val Val Thr Gly Val Val Val Arg
    370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
            435                 440                 445

Ser Leu Pro Thr Leu Leu Gln Glu Val Leu His Leu Arg Arg Gln
450                 455                 460

Leu Gln Leu Leu Lys Arg Cys Gln Glu Asn Lys Glu Glu Asp Asp Leu
465                 470                 475                 480

Ala Ala Pro Ala Tyr
            485

<210> SEQ ID NO 3
<211> LENGTH: 485
<212> TYPE: PRT
<213> ORGANISM: Artificial Sequence
<220> FEATURE:
<223> OTHER INFORMATION: E52K

<400> SEQUENCE: 3

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Lys Pro Ala Tyr Cys Gly Leu Ala Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
            100                 105                 110

```
Cys Ser Gly Ala Lys Val Glu Ala Phe Arg Thr Ser Gln Ser Thr Ile
            115                 120                 125

Asp Asp Phe Arg Lys Phe Val Lys Cys Thr Ser Ser Glu Asn Cys
130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Val Arg
370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Glu Val Leu His Leu Arg Arg Gln
450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 4
<211> LENGTH: 485
<212> TYPE: PRT
<213> ORGANISM: Artificial Sequence
<220> FEATURE:
<223> OTHER INFORMATION: A59V
```

<400> SEQUENCE: 4

Met Ala Met Ala Ser Leu Tyr Arg Arg Ser Leu Pro Ser Pro Pro Ala
1               5                  10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Val Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Val Lys Cys Thr Ser Ser Glu Asn Cys
    130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Val Arg
    370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val

-continued

```
                        405                 410                 415
Phe Thr Ala Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
            435                 440                 445

Ser Leu Pro Thr Leu Leu Gln Glu Glu Val Leu His Leu Arg Arg Gln
450                 455                 460

Leu Gln Leu Leu Lys Arg Cys Gln Glu Asn Lys Glu Glu Asp Asp Leu
465                 470                 475                 480

Ala Ala Pro Ala Tyr
            485

<210> SEQ ID NO 5
<211> LENGTH: 485
<212> TYPE: PRT
<213> ORGANISM: Artificial Sequence
<220> FEATURE:
<223> OTHER INFORMATION: D71N

<400> SEQUENCE: 5

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
                20                  25                  30

Gln Lys Gly Thr Met Glu Gly Phe Phe Arg Leu Ile Ser Tyr Phe Gln
            35                  40                  45

Thr Gln Ser Glu Pro Ala Tyr Cys Gly Leu Ala Ser Leu Ser Val Val
        50                  55                  60

Leu Asn Ala Leu Ser Ile Asn Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Val Lys Cys Thr Ser Ser Glu Asn Cys
130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
```

```
              275                 280                 285
Asp Ser Asn Gln Asn Leu Ser Ala Glu Glu Lys Ser Arg Leu Lys Leu
290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
                340                 345                 350

Pro Ser Lys Glu Phe Cys Cys Arg Glu Thr Cys Val Lys Cys Ile Lys
                355                 360                 365

Gly Pro Asp Asp Ser Glu Gly Thr Val Val Thr Gly Val Val Val Arg
370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
                420                 425                 430

Lys Asp Gln Ala Leu Met His Glu Met Lys Gln Leu Ile Ser Met Ala
                435                 440                 445

Ser Leu Pro Thr Leu Leu Gln Glu Glu Val Leu His Leu Arg Arg Gln
450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 6
<211> LENGTH: 485
<212> TYPE: PRT
<213> ORGANISM: Artificial Sequence
<220> FEATURE:
<223> OTHER INFORMATION: V97C

<400> SEQUENCE: 6

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
                20                  25                  30

Gln Lys Gly Thr Met Glu Gly Phe Phe Arg Leu Ile Ser Tyr Phe Gln
            35                  40                  45

Thr Gln Ser Glu Pro Ala Tyr Cys Gly Leu Ala Ser Leu Ser Val Val
        50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Cys Lys Glu Lys Gly Ile Ser Phe Gly Lys Val Val Cys Leu Ala His
                100                 105                 110

Cys Ser Gly Ala Lys Val Glu Ala Phe Arg Thr Ser Gln Ser Thr Ile
            115                 120                 125

Asp Asp Phe Arg Lys Phe Val Val Lys Cys Thr Ser Ser Glu Asn Cys
        130                 135                 140

His Met Ile Ser Thr Tyr His Arg Gly Val Phe Lys Gln Thr Gly Thr
```

-continued

```
            145                 150                 155                 160
Gly His Phe Ser Pro Ile Gly Gly Tyr Asn Ala Glu Arg Asp Met Ala
                    165                 170                 175

Leu Ile Leu Asp Val Ala Arg Phe Lys Tyr Pro Pro His Trp Val Pro
                180                 185                 190

Leu Lys Leu Leu Trp Glu Ala Met Asp Ser Ile Asp Gln Ser Thr Gly
            195                 200                 205

Lys Arg Arg Gly Phe Met Leu Ile Ser Arg Pro His Arg Glu Pro Gly
        210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Val Arg
    370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 7
<211> LENGTH: 485
<212> TYPE: PRT
<213> ORGANISM: Artificial Sequence
<220> FEATURE:
<223> OTHER INFORMATION: T139P

<400> SEQUENCE: 7

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
```

-continued

```
                     20                  25                  30
     Gln Lys Gly Thr Met Glu Gly Phe Phe Arg Leu Ile Ser Tyr Phe Gln
                     35                  40                  45

Thr Gln Ser Glu Pro Ala Tyr Cys Gly Leu Ala Ser Leu Ser Val Val
                     50                  55                  60

Leu Asn Ala Leu Ser Ile Asp Pro Gly Arg Lys Trp Lys Gly Pro Trp
     65                  70                  75                  80

Arg Trp Phe Asp Glu Ser Met Leu Asp Cys Cys Glu Pro Leu Glu Val
                         85                  90                  95

Val Lys Glu Lys Gly Ile Ser Phe Gly Lys Val Val Cys Leu Ala His
                     100                 105                 110

Cys Ser Gly Ala Lys Val Glu Ala Phe Arg Thr Ser Gln Ser Thr Ile
                     115                 120                 125

Asp Asp Phe Arg Lys Phe Val Val Lys Cys Pro Ser Ser Glu Asn Cys
                     130                 135                 140

His Met Ile Ser Thr Tyr His Arg Gly Val Phe Lys Gln Thr Gly Thr
     145                 150                 155                 160

Gly His Phe Ser Pro Ile Gly Gly Tyr Asn Ala Glu Arg Asp Met Ala
                         165                 170                 175

Leu Ile Leu Asp Val Ala Arg Phe Lys Tyr Pro Pro His Trp Val Pro
                     180                 185                 190

Leu Lys Leu Leu Trp Glu Ala Met Asp Ser Ile Asp Gln Ser Thr Gly
                     195                 200                 205

Lys Arg Arg Gly Phe Met Leu Ile Ser Arg Pro His Arg Glu Pro Gly
                     210                 215                 220

Leu Leu Tyr Thr Leu Ser Cys Lys Asp Glu Ser Trp Ile Glu Ile Ala
     225                 230                 235                 240

Lys Tyr Leu Lys Glu Asp Val Pro Arg Leu Val Ser Ser Gln His Val
                         245                 250                 255

Asp Ser Val Glu Lys Ile Ile Ser Val Val Phe Lys Ser Leu Pro Ser
                     260                 265                 270

Asn Phe Asn Gln Phe Ile Arg Trp Val Ala Glu Ile Arg Ile Thr Glu
                     275                 280                 285

Asp Ser Asn Gln Asn Leu Ser Ala Glu Lys Ser Arg Leu Lys Leu
                     290                 295                 300

Lys Gln Leu Val Leu Lys Glu Val His Glu Thr Glu Leu Phe Lys His
     305                 310                 315                 320

Ile Asn Lys Phe Leu Ser Thr Val Gly Tyr Glu Asp Ser Leu Thr Tyr
                         325                 330                 335

Ala Ala Ala Lys Ala Cys Cys Gln Gly Ala Glu Ile Leu Ser Gly Ser
                     340                 345                 350

Pro Ser Lys Glu Phe Cys Cys Arg Glu Thr Cys Val Lys Cys Ile Lys
                     355                 360                 365

Gly Pro Asp Asp Ser Glu Gly Thr Val Val Thr Gly Val Val Arg
                     370                 375                 380

Asp Gly Asn Glu Gln Lys Val Asp Leu Leu Val Pro Ser Thr Gln Thr
     385                 390                 395                 400

Glu Cys Glu Cys Gly Pro Glu Ala Thr Tyr Pro Ala Gly Asn Asp Val
                         405                 410                 415

Phe Thr Ala Leu Leu Leu Ala Leu Pro Pro Gln Thr Trp Ser Gly Ile
                     420                 425                 430

Lys Asp Gln Ala Leu Met His Glu Met Lys Gln Leu Ile Ser Met Ala
                     435                 440                 445
```

```
Ser Leu Pro Thr Leu Leu Gln Glu Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480

Ala Ala Pro Ala Tyr
            485

<210> SEQ ID NO 8
<211> LENGTH: 485
<212> TYPE: PRT
<213> ORGANISM: Artificial Sequence
<220> FEATURE:
<223> OTHER INFORMATION: V181G

<400> SEQUENCE: 8

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Ala Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Val Lys Cys Thr Ser Ser Glu Asn Cys
    130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Gly Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320
```

```
Ile Asn Lys Phe Leu Ser Thr Val Gly Tyr Glu Asp Ser Leu Thr Tyr
            325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
            355                 360                 365

Gly Pro Asp Asp Ser Glu Gly Thr Val Val Thr Gly Val Val Arg
370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                    405                 410                 415

Phe Thr Ala Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
            435                 440                 445

Ser Leu Pro Thr Leu Leu Gln Glu Val Leu His Leu Arg Arg Gln
            450                 455                 460

Leu Gln Leu Leu Lys Arg Cys Gln Glu Asn Lys Glu Glu Asp Asp Leu
465                 470                 475                 480

Ala Ala Pro Ala Tyr
            485

<210> SEQ ID NO 9
<211> LENGTH: 485
<212> TYPE: PRT
<213> ORGANISM: Artificial Sequence
<220> FEATURE:
<223> OTHER INFORMATION: Y186C

<400> SEQUENCE: 9

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Arg Leu Ile Ser Tyr Phe Gln
            35                  40                  45

Thr Gln Ser Glu Pro Ala Tyr Cys Gly Leu Ala Ser Leu Ser Val Val
            50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                    85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
            115                 120                 125

Asp Asp Phe Arg Lys Phe Val Val Lys Cys Thr Ser Ser Glu Asn Cys
130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                    165                 170                 175

Leu Ile Leu Asp Val Ala Arg Phe Lys Cys Pro Pro His Trp Val Pro
            180                 185                 190
```

```
Leu Lys Leu Leu Trp Glu Ala Met Asp Ser Ile Asp Gln Ser Thr Gly
        195                 200                 205
Lys Arg Arg Gly Phe Met Leu Ile Ser Arg Pro His Arg Glu Pro Gly
    210                 215                 220
Leu Leu Tyr Thr Leu Ser Cys Lys Asp Glu Ser Trp Ile Glu Ile Ala
225                 230                 235                 240
Lys Tyr Leu Lys Glu Asp Val Pro Arg Leu Val Ser Ser Gln His Val
                245                 250                 255
Asp Ser Val Glu Lys Ile Ile Ser Val Val Phe Lys Ser Leu Pro Ser
            260                 265                 270
Asn Phe Asn Gln Phe Ile Arg Trp Val Ala Glu Ile Arg Ile Thr Glu
        275                 280                 285
Asp Ser Asn Gln Asn Leu Ser Ala Glu Glu Lys Ser Arg Leu Lys Leu
    290                 295                 300
Lys Gln Leu Val Leu Lys Glu Val His Glu Thr Glu Leu Phe Lys His
305                 310                 315                 320
Ile Asn Lys Phe Leu Ser Thr Val Gly Tyr Glu Asp Ser Leu Thr Tyr
                325                 330                 335
Ala Ala Ala Lys Ala Cys Cys Gln Gly Ala Glu Ile Leu Ser Gly Ser
            340                 345                 350
Pro Ser Lys Glu Phe Cys Cys Arg Glu Thr Cys Val Lys Cys Ile Lys
        355                 360                 365
Gly Pro Asp Asp Ser Glu Gly Thr Val Val Thr Gly Val Val Val Arg
    370                 375                 380
Asp Gly Asn Glu Gln Lys Val Asp Leu Leu Val Pro Ser Thr Gln Thr
385                 390                 395                 400
Glu Cys Glu Cys Gly Pro Glu Ala Thr Tyr Pro Ala Gly Asn Asp Val
                405                 410                 415
Phe Thr Ala Leu Leu Leu Ala Leu Pro Pro Gln Thr Trp Ser Gly Ile
            420                 425                 430
Lys Asp Gln Ala Leu Met His Glu Met Lys Gln Leu Ile Ser Met Ala
        435                 440                 445
Ser Leu Pro Thr Leu Leu Gln Glu Glu Val Leu His Leu Arg Arg Gln
    450                 455                 460
Leu Gln Leu Leu Lys Arg Cys Gln Glu Asn Lys Glu Glu Asp Asp Leu
465                 470                 475                 480
Ala Ala Pro Ala Tyr
                485

<210> SEQ ID NO 10
<211> LENGTH: 485
<212> TYPE: PRT
<213> ORGANISM: Artificial Sequence
<220> FEATURE:
<223> OTHER INFORMATION: S60C_S202I

<400> SEQUENCE: 10

Met Ala Met Ala Ser Leu Tyr Arg Arg Ser Leu Pro Ser Pro Pro Ala
1               5                   10                  15
Ile Asp Phe Ser Ser Ala Glu Gly Lys Leu Ile Phe Asn Glu Ala Leu
            20                  25                  30
Gln Lys Gly Thr Met Glu Gly Phe Phe Arg Leu Ile Ser Tyr Phe Gln
        35                  40                  45
Thr Gln Ser Glu Pro Ala Tyr Cys Gly Leu Ala Cys Leu Ser Val Val
    50                  55                  60
```

```
Leu Asn Ala Leu Ser Ile Asp Pro Gly Arg Lys Trp Lys Gly Pro Trp
 65                  70                  75                  80

Arg Trp Phe Asp Glu Ser Met Leu Asp Cys Cys Glu Pro Leu Glu Val
                 85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Val Lys Cys Thr Ser Ser Glu Asn Cys
    130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ile Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Val Arg
    370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480
```

Ala Ala Pro Ala Tyr
            485

<210> SEQ ID NO 11
<211> LENGTH: 485
<212> TYPE: PRT
<213> ORGANISM: Artificial Sequence
<220> FEATURE:
<223> OTHER INFORMATION: C109Y

<400> SEQUENCE: 11

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Ala Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Tyr Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Lys Cys Thr Ser Ser Glu Asn Cys
    130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

```
Pro Ser Lys Glu Phe Cys Cys Arg Glu Thr Cys Val Lys Cys Ile Lys
            355                 360                 365

Gly Pro Asp Asp Ser Glu Gly Thr Val Val Thr Gly Val Val Val Arg
370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 12
<211> LENGTH: 485
<212> TYPE: PRT
<213> ORGANISM: Artificial Sequence
<220> FEATURE:
<223> OTHER INFORMATION: T123R_F163I

<400> SEQUENCE: 12

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Ala Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Arg Ser Gln Ser Thr Ile
        115                 120                 125

Asp Asp Phe Arg Lys Phe Val Val Lys Cys Thr Ser Ser Glu Asn Cys
130                 135                 140

His Met Ile Ser Thr Tyr His Arg Gly Val Phe Lys Gln Thr Gly Thr
145                 150                 155                 160

Gly His Ile Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220
```

-continued

```
Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
            245                 250                 255

Asp Ser Val Glu Lys Ile Ile Ser Val Val Phe Lys Ser Leu Pro Ser
        260                 265                 270

Asn Phe Asn Gln Phe Ile Arg Trp Val Ala Glu Ile Arg Ile Thr Glu
    275                 280                 285

Asp Ser Asn Gln Asn Leu Ser Ala Glu Glu Lys Ser Arg Leu Lys Leu
290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Arg
370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 13
<211> LENGTH: 485
<212> TYPE: PRT
<213> ORGANISM: Artificial Sequence
<220> FEATURE:
<223> OTHER INFORMATION: C91S_A199S

<400> SEQUENCE: 13

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Ala Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Ser Glu Pro Leu Glu Val
                85                  90                  95
```

-continued

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Lys Cys Thr Ser Ser Glu Asn Cys
    130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ser Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Arg
    370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 14
<211> LENGTH: 485
<212> TYPE: PRT

<213> ORGANISM: Artificial Sequence
<220> FEATURE:
<223> OTHER INFORMATION: F83C_N170D

<400> SEQUENCE: 14

```
Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Ala Ser Leu Ser Val Val
50                  55                  60

Leu Asn Ala Leu Ser Ile Asp Pro Gly Arg Lys Trp Lys Gly Pro Trp
65                  70                  75                  80

Arg Trp Cys Asp Glu Ser Met Leu Asp Cys Cys Glu Pro Leu Glu Val
            85                  90                  95

Val Lys Glu Lys Gly Ile Ser Phe Gly Lys Val Val Cys Leu Ala His
        100                 105                 110

Cys Ser Gly Ala Lys Val Glu Ala Phe Arg Thr Ser Gln Ser Thr Ile
    115                 120                 125

Asp Asp Phe Arg Lys Phe Val Val Lys Cys Thr Ser Ser Glu Asn Cys
130                 135                 140

His Met Ile Ser Thr Tyr His Arg Gly Val Phe Lys Gln Thr Gly Thr
145                 150                 155                 160

Gly His Phe Ser Pro Ile Gly Gly Tyr Asp Ala Glu Arg Asp Met Ala
            165                 170                 175

Leu Ile Leu Asp Val Ala Arg Phe Lys Tyr Pro Pro His Trp Val Pro
        180                 185                 190

Leu Lys Leu Leu Trp Glu Ala Met Asp Ser Ile Asp Gln Ser Thr Gly
    195                 200                 205

Lys Arg Arg Gly Phe Met Leu Ile Ser Arg Pro His Arg Glu Pro Gly
210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
            245                 250                 255

Asp Ser Val Glu Lys Ile Ile Ser Val Val Phe Lys Ser Leu Pro Ser
        260                 265                 270

Asn Phe Asn Gln Phe Ile Arg Trp Val Ala Glu Ile Arg Ile Thr Glu
    275                 280                 285

Asp Ser Asn Gln Asn Leu Ser Ala Glu Glu Lys Ser Arg Leu Lys Leu
290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Gly Asp Ser Leu Thr Tyr
            325                 330                 335

Ala Ala Ala Lys Ala Cys Cys Gln Gly Ala Glu Ile Leu Ser Gly Ser
        340                 345                 350

Pro Ser Lys Glu Phe Cys Cys Arg Glu Thr Cys Val Lys Cys Ile Lys
    355                 360                 365

Gly Pro Asp Asp Ser Glu Gly Thr Val Val Thr Gly Val Val Val Arg
370                 375                 380

Asp Gly Asn Glu Gln Lys Val Asp Leu Leu Val Pro Ser Thr Gln Thr
```

```
385                 390                 395                 400
Glu Cys Glu Cys Gly Pro Glu Ala Thr Tyr Pro Ala Gly Asn Asp Val
                405                 410                 415
Phe Thr Ala Leu Leu Ala Leu Pro Pro Gln Thr Trp Ser Gly Ile
                420                 425                 430
Lys Asp Gln Ala Leu Met His Glu Met Lys Gln Leu Ile Ser Met Ala
                435                 440                 445
Ser Leu Pro Thr Leu Leu Gln Glu Glu Val Leu His Leu Arg Arg Gln
        450                 455                 460
Leu Gln Leu Leu Lys Arg Cys Gln Glu Asn Lys Glu Glu Asp Asp Leu
465                 470                 475                 480
Ala Ala Pro Ala Tyr
                485

<210> SEQ ID NO 15
<211> LENGTH: 485
<212> TYPE: PRT
<213> ORGANISM: Artificial Sequence
<220> FEATURE:
<223> OTHER INFORMATION: A182G_A282V_G329S

<400> SEQUENCE: 15

Met Ala Met Ala Ser Leu Tyr Arg Arg Ser Leu Pro Ser Pro Pro Ala
1               5                   10                  15
Ile Asp Phe Ser Ser Ala Glu Gly Lys Leu Ile Phe Asn Glu Ala Leu
                20                  25                  30
Gln Lys Gly Thr Met Gly Phe Phe Arg Leu Ile Ser Tyr Phe Gln
            35                  40                  45
Thr Gln Ser Glu Pro Ala Tyr Cys Gly Leu Ala Ser Leu Ser Val Val
        50                  55                  60
Leu Asn Ala Leu Ser Ile Asp Pro Gly Arg Lys Trp Lys Gly Pro Trp
65                  70                  75                  80
Arg Trp Phe Asp Glu Ser Met Leu Asp Cys Cys Glu Pro Leu Glu Val
                85                  90                  95
Val Lys Glu Lys Gly Ile Ser Phe Gly Lys Val Val Cys Leu Ala His
                100                 105                 110
Cys Ser Gly Ala Lys Val Glu Ala Phe Arg Thr Ser Gln Ser Thr Ile
            115                 120                 125
Asp Asp Phe Arg Lys Phe Val Val Lys Cys Thr Ser Ser Glu Asn Cys
        130                 135                 140
His Met Ile Ser Thr Tyr His Arg Gly Val Phe Lys Gln Thr Gly Thr
145                 150                 155                 160
Gly His Phe Ser Pro Ile Gly Gly Tyr Asn Ala Glu Arg Asp Met Ala
                165                 170                 175
Leu Ile Leu Asp Val Gly Arg Phe Lys Tyr Pro Pro His Trp Val Pro
                180                 185                 190
Leu Lys Leu Leu Trp Glu Ala Met Asp Ser Ile Asp Gln Ser Thr Gly
            195                 200                 205
Lys Arg Arg Gly Phe Met Leu Ile Ser Arg Pro His Arg Glu Pro Gly
        210                 215                 220
Leu Leu Tyr Thr Leu Ser Cys Lys Asp Glu Ser Trp Ile Glu Ile Ala
225                 230                 235                 240
Lys Tyr Leu Lys Glu Asp Val Pro Arg Leu Val Ser Ser Gln His Val
                245                 250                 255
Asp Ser Val Glu Lys Ile Ile Ser Val Val Phe Lys Ser Leu Pro Ser
```

```
            260                 265                 270
Asn Phe Asn Gln Phe Ile Arg Trp Val Val Glu Ile Arg Ile Thr Glu
                275                 280                 285

Asp Ser Asn Gln Asn Leu Ser Ala Glu Glu Lys Ser Arg Leu Lys Leu
290                 295                 300

Lys Gln Leu Val Leu Lys Glu Val His Glu Thr Glu Leu Phe Lys His
305                 310                 315                 320

Ile Asn Lys Phe Leu Ser Thr Val Ser Tyr Glu Asp Ser Leu Thr Tyr
                325                 330                 335

Ala Ala Ala Lys Ala Cys Cys Gln Gly Ala Glu Ile Leu Ser Gly Ser
                340                 345                 350

Pro Ser Lys Glu Phe Cys Cys Arg Glu Thr Cys Val Lys Cys Ile Lys
                355                 360                 365

Gly Pro Asp Asp Ser Glu Gly Thr Val Val Thr Gly Val Val Val Arg
        370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                    405                 410                 415

Phe Thr Ala Leu Leu Leu Ala Leu Pro Pro Gln Thr Trp Ser Gly Ile
                420                 425                 430

Lys Asp Gln Ala Leu Met His Glu Met Lys Gln Leu Ile Ser Met Ala
                435                 440                 445

Ser Leu Pro Thr Leu Leu Gln Glu Glu Val Leu His Leu Arg Arg Gln
450                 455                 460

Leu Gln Leu Leu Lys Arg Cys Gln Glu Asn Lys Glu Asp Asp Leu
465                 470                 475                 480

Ala Ala Pro Ala Tyr
                485

<210> SEQ ID NO 16
<211> LENGTH: 485
<212> TYPE: PRT
<213> ORGANISM: Artificial Sequence
<220> FEATURE:
<223> OTHER INFORMATION: R74H_S230C_L250R

<400> SEQUENCE: 16

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
                20                  25                  30

Gln Lys Gly Thr Met Glu Gly Phe Phe Arg Leu Ile Ser Tyr Phe Gln
            35                  40                  45

Thr Gln Ser Glu Pro Ala Tyr Cys Gly Leu Ala Ser Leu Ser Val Val
50                  55                  60

Leu Asn Ala Leu Ser Ile Asp Pro Gly His Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
                100                 105                 110

Cys Ser Gly Ala Lys Val Glu Ala Phe Arg Thr Ser Gln Ser Thr Ile
            115                 120                 125

Asp Asp Phe Arg Lys Phe Val Val Lys Cys Thr Ser Ser Glu Asn Cys
```

```
                130                 135                 140
His Met Ile Ser Thr Tyr His Arg Gly Val Phe Lys Gln Thr Gly Thr
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Cys Cys Lys Asp Glu Ser Trp Ile Glu Ile Ala
225                 230                 235                 240

Lys Tyr Leu Lys Glu Asp Val Pro Arg Val Ser Ser Gln His Val
                245                 250                 255

Asp Ser Val Glu Lys Ile Ile Ser Val Val Phe Lys Ser Leu Pro Ser
            260                 265                 270

Asn Phe Asn Gln Phe Ile Arg Trp Val Ala Glu Ile Arg Ile Thr Glu
        275                 280                 285

Asp Ser Asn Gln Asn Leu Ser Ala Glu Glu Lys Ser Arg Leu Lys Leu
    290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Arg
    370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480

Ala Ala Pro Ala Tyr
                485

<210> SEQ ID NO 17
<211> LENGTH: 485
<212> TYPE: PRT
<213> ORGANISM: Artificial Sequence
<220> FEATURE:
<223> OTHER INFORMATION: S51T_N143I_N170I_H220R

<400> SEQUENCE: 17

Met Ala Met Ala Ser Leu Tyr Arg Arg Ser Leu Pro Ser Pro Pro Ala
```

-continued

```
1               5                   10                  15
Ile Asp Phe Ser Ser Ala Glu Gly Lys Leu Ile Phe Asn Glu Ala Leu
                20                  25                  30
Gln Lys Gly Thr Met Glu Gly Phe Phe Arg Leu Ile Ser Tyr Phe Gln
                35                  40                  45
Thr Gln Thr Glu Pro Ala Tyr Cys Gly Leu Ala Ser Leu Ser Val Val
                50                  55                  60
Leu Asn Ala Leu Ser Ile Asp Pro Gly Arg Lys Trp Lys Gly Pro Trp
65                  70                  75                  80
Arg Trp Phe Asp Glu Ser Met Leu Asp Cys Cys Glu Pro Leu Glu Val
                85                  90                  95
Val Lys Glu Lys Gly Ile Ser Phe Gly Lys Val Val Cys Leu Ala His
                100                 105                 110
Cys Ser Gly Ala Lys Val Glu Ala Phe Arg Thr Ser Gln Ser Thr Ile
                115                 120                 125
Asp Asp Phe Arg Lys Phe Val Val Lys Cys Thr Ser Ser Glu Ile Cys
                130                 135                 140
His Met Ile Ser Thr Tyr His Arg Gly Val Phe Lys Gln Thr Gly Thr
145                 150                 155                 160
Gly His Phe Ser Pro Ile Gly Gly Tyr Ile Ala Glu Arg Asp Met Ala
                165                 170                 175
Leu Ile Leu Asp Val Ala Arg Phe Lys Tyr Pro Pro His Trp Val Pro
                180                 185                 190
Leu Lys Leu Leu Trp Glu Ala Met Asp Ser Ile Asp Gln Ser Thr Gly
                195                 200                 205
Lys Arg Arg Gly Phe Met Leu Ile Ser Arg Pro Arg Glu Pro Gly
                210                 215                 220
Leu Leu Tyr Thr Leu Ser Cys Lys Asp Glu Ser Trp Ile Glu Ile Ala
225                 230                 235                 240
Lys Tyr Leu Lys Glu Asp Val Pro Arg Leu Val Ser Ser Gln His Val
                245                 250                 255
Asp Ser Val Glu Lys Ile Ile Ser Val Val Phe Lys Ser Leu Pro Ser
                260                 265                 270
Asn Phe Asn Gln Phe Ile Arg Trp Val Ala Glu Ile Arg Ile Thr Glu
                275                 280                 285
Asp Ser Asn Gln Asn Leu Ser Ala Glu Glu Lys Ser Arg Leu Lys Leu
                290                 295                 300
Lys Gln Leu Val Leu Lys Glu Val His Glu Thr Glu Leu Phe Lys His
305                 310                 315                 320
Ile Asn Lys Phe Leu Ser Thr Val Gly Tyr Glu Asp Ser Leu Thr Tyr
                325                 330                 335
Ala Ala Ala Lys Ala Cys Cys Gln Gly Ala Glu Ile Leu Ser Gly Ser
                340                 345                 350
Pro Ser Lys Glu Phe Cys Cys Arg Glu Thr Cys Val Lys Cys Ile Lys
                355                 360                 365
Gly Pro Asp Asp Ser Glu Gly Thr Val Val Thr Gly Val Val Val Arg
                370                 375                 380
Asp Gly Asn Glu Gln Lys Val Asp Leu Leu Val Pro Ser Thr Gln Thr
385                 390                 395                 400
Glu Cys Glu Cys Gly Pro Glu Ala Thr Tyr Pro Ala Gly Asn Asp Val
                405                 410                 415
Phe Thr Ala Leu Leu Leu Ala Leu Pro Pro Gln Thr Trp Ser Gly Ile
                420                 425                 430
```

Lys Asp Gln Ala Leu Met His Glu Met Lys Gln Leu Ile Ser Met Ala
            435                 440                 445

Ser Leu Pro Thr Leu Leu Gln Glu Glu Val Leu His Leu Arg Arg Gln
            450                 455                 460

Leu Gln Leu Leu Lys Arg Cys Gln Glu Asn Lys Glu Glu Asp Asp Leu
465                 470                 475                 480

Ala Ala Pro Ala Tyr
            485

<210> SEQ ID NO 18
<211> LENGTH: 485
<212> TYPE: PRT
<213> ORGANISM: Artificial Sequence
<220> FEATURE:
<223> OTHER INFORMATION: Q48R_C144Y_G168S_W280R

<400> SEQUENCE: 18

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Arg
            35                  40                  45

Thr Gln Ser Glu Pro Ala Tyr Cys Gly Leu Ala Ser Leu Ser Val Val
50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
            85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
            115                 120                 125

Asp Asp Phe Arg Lys Phe Val Val Lys Cys Thr Ser Ser Glu Asn Tyr
            130                 135                 140

His Met Ile Ser Thr Tyr His Arg Gly Val Phe Lys Gln Thr Gly Thr
145                 150                 155                 160

Gly His Phe Ser Pro Ile Ser Gly Tyr Asn Ala Glu Arg Asp Met Ala
            165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
            195                 200                 205

Lys Arg Arg Gly Phe Met Leu Ile Ser Arg Pro His Arg Glu Pro Gly
            210                 215                 220

Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
            245                 250                 255

Asp Ser Val Glu Lys Ile Ile Ser Val Val Phe Lys Ser Leu Pro Ser
            260                 265                 270

Asn Phe Asn Gln Phe Ile Arg Arg Val Ala Glu Ile Arg Ile Thr Glu
            275                 280                 285

Asp Ser Asn Gln Asn Leu Ser Ala Glu Glu Lys Ser Arg Leu Lys Leu
            290                 295                 300

```
Lys Gln Leu Val Leu Lys Glu Val His Glu Thr Glu Leu Phe Lys His
305                 310                 315                 320
Ile Asn Lys Phe Leu Ser Thr Val Gly Tyr Glu Asp Ser Leu Thr Tyr
                325                 330                 335
Ala Ala Ala Lys Ala Cys Cys Gln Gly Ala Glu Ile Leu Ser Gly Ser
            340                 345                 350
Pro Ser Lys Glu Phe Cys Cys Arg Glu Thr Cys Val Lys Cys Ile Lys
        355                 360                 365
Gly Pro Asp Asp Ser Glu Gly Thr Val Val Thr Gly Val Val Val Arg
    370                 375                 380
Asp Gly Asn Glu Gln Lys Val Asp Leu Leu Val Pro Ser Thr Gln Thr
385                 390                 395                 400
Glu Cys Glu Cys Gly Pro Glu Ala Thr Tyr Pro Ala Gly Asn Asp Val
            405                 410                 415
Phe Thr Ala Leu Leu Leu Ala Leu Pro Pro Gln Thr Trp Ser Gly Ile
            420                 425                 430
Lys Asp Gln Ala Leu Met His Glu Met Lys Gln Leu Ile Ser Met Ala
        435                 440                 445
Ser Leu Pro Thr Leu Leu Gln Glu Glu Val Leu His Leu Arg Arg Gln
    450                 455                 460
Leu Gln Leu Leu Lys Arg Cys Gln Glu Asn Lys Glu Glu Asp Asp Leu
465                 470                 475                 480
Ala Ala Pro Ala Tyr
            485
```

TRANSGENIC PLANTS EXHIBITING ENHANCED PHYTOCHELATIN-BASED HEAVY METAL TOLERANCE AND METHODS OF USE THEREOF

This application claims priority to U.S. Provisional Application No. 62/340,931 filed May 24, 2016, the entire contents being incorporated herein by reference as though set forth in full.

This invention was made with government support under Grant Numbers EPA-X-83220101, NRI-2005-02518, MCB-0904215, and DE-FG02-91ER2005 awarded by the Environmental Protection Agency, United States Department of Agriculture, National Science Foundation and United States Department of Energy, respectively. The government has certain rights in the invention.

FIELD OF THE INVENTION

The present invention relates to the fields of transgenic plants and remediation of contaminated soil and ground water. More specifically, the invention provides transgenic plants over-expressing *Arabidopsis thaliana* phytochelatin synthase 1 (AtPCS1) mutant proteins and methods of use thereof for increasing cadmium and other heavy metal tolerance and accumulation.

BACKGROUND OF THE INVENTION

Several publications and patent documents are cited throughout the specification in order to describe the state of the art to which this invention pertains. Each of these citations is incorporated by reference herein as though set forth in full.

Environmental heavy metal contamination, which is implicated in many diseases and agricultural losses (1-2), poses a challenge with a price tag for remediation estimated at upward of $200 billion in the US alone (2). Heavy metals, such as cadmium ($Cd^{2+}$), undergo aberrant capping reactions with the thiol groups of proteins and some coenzymes, displace endogenous metal cofactors from their cellular binding sites, and promote the formation of reactive oxygen species (2). Engineering plants and microbes for the detoxification of heavy metal contaminated soils and waters traditionally relies on the modification of existing metabolic pathways and/or metal transport and sequestration systems (3-7). Although transgenic methods can enhance heavy metal tolerance and accumulation, the inherent biochemical properties of the proteins introduced often limit the extent of the enhancement. Engineering the proteins that are used for this purpose can offset inherent limitations on tolerance to and/or accumulation of heavy metals so as to broaden the range of molecular tools available for environmental clean-up (8). An objective of the present invention is to provide such plants and methods of use thereof for environmental bioremediation.

SUMMARY OF THE INVENTION

In accordance with the present invention, several isolated nucleic acids encoding variant phytochelatin synthase (PCS) enzymes are disclosed, wherein the synthase exhibits diminished catalytic activity and is provided in Table 1. In preferred embodiment, the variant comprises a Y186C substitution or a C109Y substitution. The vector encoding the nucleic acids may further comprise additional regulatory elements that promote and/or stabilize expression of the transgene. The vectors may also comprise a reporter nucleic acid. In yet another embodiment, plant cells comprising the vectors described above are provided. While variant PCS enzymes from plants are exemplified herein, any variant PCS which exhibits diminished enzyme activity while enhancing heavy metal tolerance is within the scope of the invention.

In particularly preferred embodiment, a transgenic plant stably transformed with an isolated nucleic acid encoding a variant PCS is disclosed. Cells, seeds or progeny of the stably transformed plant also form an aspect of the invention.

Also within the scope of the invention is a method of producing transgenic heavy metal resistant plants comprising introducing nucleic acids encoding the PCS variants into cells of the plant, thereby conferring heavy metal resistance to the plant.

In another aspect, a method of decreasing the level of a heavy metal in a harvestable portion of a plant is provided. An exemplary method comprising expressing the nucleic acid encoding the variant PCS in a non-harvestable portion of a plant, thereby decreasing the level of heavy metal in the harvestable portion of the plant.

Also encompassed by the present invention, is a method of removing a heavy metal from groundwater, the method comprising growing the PCS variant expressing transgenic plant in contaminated groundwater, and harvesting the plant from the groundwater, thereby removing heavy metal from groundwater.

The application file contains at least one drawing executed in color. Copies of this patent or patent application publication with color drawing(s) will be provided by the Office upon request and payment of the necessary fee.

BRIEF DESCRIPTION OF THE DRAWING

FIG. 1A. General structure of a representative phytochelatin (PC). The example shown is $PC_2$, which contains two γ-glutamylcysteine (γEC) repeats. The core structures of PCs consist of 2-15 γEC repeats derived from glutathione (GSH) by the transfer of a γEC unit from one GSH molecule to another or by the transfer of γEC units from GSH to preexistent PCs. PCs have the general structure $(γEC)_nX$, where X is usually Gly. FIG. 1B. The overall reaction catalyzed by PCS is a heavy metal, for instance $Cd^{2+}$—, activated dipeptidyl transfer reaction in which PC chain extension proceeds in the N to C direction.

FIG. 2A. $Cd^{2+}$ sensitivity of *S. cerevisiae* ycf1Δ strain DTY167 transformed with empty pYES3 vector (Vec), pYES3-AtPCS1::FLAG construct containing wild-type AtPCS1 (AtPCS1), or pYES3-AtPCS1::FLAG constructs carrying AtPCS1 mutations. FIG. 2B. RP-HPLC analysis of PCs extracted from yeast strain DTY167 transformed with pYES3-AtPCS1::FLAG (blue) or pYES3-AtPCS1-Y186C::FLAG (red) after growth for 2 h in liquid media containing 250 μM $CdCl_2$. Peaks labeled as $PC_{2-5}$ were identified by MALDI-TOF MS in negative ion mode. FIG. 2C. Western analysis of FLAG-tag in yeast strain DTY167 transformants expressing wild-type or mutant AtPCS1::FLAG. Aliquots (20 μg protein) of the soluble fractions were separated by SDS-PAGE, electrotransferred to nitrocellulose membranes, and probed with anti-FLAG M2 antibody. The $M_r$ 55,000 AtPCS1::FLAG polypeptide was the major immunoreactive band. FIG. 2D. Comparison of cellular $Cd^{2+}$ contents of yeast strain DTY167 transformed with empty pYES3 vector (white), pYES3-AtPCS1::FLAG (black), pYES3-AtPCS1-C109Y::FLAG (red) or pYES3-AtPCS1-Y186C::FLAG (blue) after growth for 24 h in liquid media containing 0, 50 or 250 µM $CdCl_2$. The histogram in the left-hand panel is $Cd^{2+}$ content (µg) per $10^7$ cells; the histogram in the right-hand panel is $Cd^{2+}$ content of the total culture cell mass. Values shown are means±SE (n=3).

FIG. 4A. Western analysis of FLAG-tagged AtPCS1 in pART27-AtPCS1::FLAG transformants (transgenic lines PCS1, PCS2, PCS3 and PCS4) and pART27-AtPCS-Y186C::FLAG transformants (transgenic lines Y186C1, Y186C2, Y186C3 and Y186C4). Equal amounts (20 µg) of the total soluble protein extracted from the seedlings were separated by SDS-PAGE, electrotransferred, and probed with anti-FLAG M2 antibody to detect FLAG-tagged protein. Plants transformed with empty pART27 vector (Vec) were used as a control. FIG. 4B. $Cd^{2+}$ sensitivity of Arabidopsis lines transformed with pART27 (Vec) or pART27-AtPCS1-Y186C::FLAG (Y186C). Seeds from T2 generation Arabidopsis transformants were germinated on standard MS plates and after 5 d, seedlings were transferred to vertical MS plates containing 0 or 200 µM $CdCl_2$ for growth for a further 14 d, after which time root length was measured. FIG. 4C. Root growth of Arabidopsis seedlings transformed with pART27 (white), pART27-AtPCS1::FLAG (green) or pART27-AtPCS1-Y186C::FLAG (blue). Seeds were germinated on standard MS plates and after 5 d, seedlings were transferred to vertical MS places containing 0, 50 or 200 µM $CdCl_2$. The growth conditions were as described in FIG. 4B. Values shown are means±SE (n=25-30). FIG. 4D. Analysis of PC contents (left) and $Cd^{2+}$ accumulation (right) of pART27 (white), pART27-AtPCS1::FLAG (green), and pART27-AtPCS1-Y186C4::FLAG (blue) transformants of Arabidopsis. Levels of $PC_{2-5}$ and $Cd^{2+}$ in the homogenates of whole seedlings were determined by RP-HPLC and atomic absorption spectrometry, respectively, after growth for 10 d on MS plates containing 100 µM $CdCl_2$. Values shown are means±SE (n=3-5).

FIG. 5A. Western analysis of AtPCS1::FLAG (transgenic lines PCS1-4) and AtPCS-Y186C::FLAG mutant (transgenic lines MUT1-4) expression in transgenic B. juncea plants. Equal amounts (20 µg) of the total soluble protein extracted from the seedlings were separated by SDS-PAGE, electrotransferred, and probed with anti-FLAG M2 antibody to detect FLAG-tagged proteins. Plants transformed with empty vector (Vec) were included as a control. FIG. 5B. $Cd^{2+}$ sensitivity of B. juncea lines transformed with pART27 (vec), pART27-AtPCS1::FLAG (PCS1) or pART27-AtPCS1-Y186C::FLAG (MUT1, MUT4). The seedlings shown are derived from seeds grown for 7 d on MS plates containing 200 µM $CdCl_2$. FIG. 5C. Root length of B. juncea seedlings transformed with pART27 (white), pART27-AtPCS1::FLAG (green) or pART27-AtPCS1-Y186C::FLAG (MUT4, blue) after growth on MS plates containing 0, 100 or 200 µM $CdCl_2$. Values shown are means±SE (n=20-30). FIG. 5D. Fresh weight comparison of B. juncea seedlings transformed with pART27 (white), pART27-AtPCS1::FLAG (green; transgenic lines PCS1-4) or pART27-AtPCS1-Y186C::FLAG (blue; transgenic lines MUT1-4). Seeds were germinated on MS plates and the seedlings transferred to MS plates containing 0, 100, or 200 µM $CdCl_2$. After 7 d, the fresh weight (FW) of each seedling was measured. Values shown are means±SE (n=20-30). FIG. 5E. Analysis of PC contents (left) and $Cd^{2+}$ accumulation (right) of pART27 (white), pART27-AtPCS1::FLAG (green), and pART27-AtPCS1-Y186C(MUT4)::FLAG (blue) transformants of B. juncea. The total levels of $PC_{2-5}$ and $Cd^{2+}$ in the homogenates of whole seedlings were determined by RP-HPLC and atomic absorption spectrometry, respectively, after growth for 7 d on MS plates containing 200 µM $CdCl_2$. Values shown are means±SE (n=3-5).

FIG. 6A. Purification of His-tagged AtPCS1. Aliquots (20 µg protein) of the soluble fractions from crude sonicates of E. coli BL21 (DE3) cells expressing His-AtPCS1 (sonicate) and of the protein after nickel-affinity (NiNTA) and size-exclusion chromatography (S200) were subjected to SDS-PAGE and stained for total protein with Coomassie Blue (BioRad). The position of His-AtPCS1 at $M_r$ 55,000 is indicated. Similar results were obtained for all of the His-tagged AtCS1 variants examined. FIG. 6B. GSH concentration-dependence of PC synthesis catalyzed by His-AtPCS1 and His-AtPCS-Y186C. The assays were performed as described and the synthesis of $PC_2$ was monitored for 10 min at 30° C. in 100 mM BTP-HEPES buffer, pH 8.0 containing 300 µM $CdCl_2$, and the indicated concentrations of GSH. FIG. 6C. Structural model of the N-terminal catalytic domain of AtPCS1. A homology model of the N-terminal domain, encompassing Leu11-Ser217, was generated from the crystal structure of the prokaryotic PCS homolog Nostoc GSH hydrolyase (25; PDB: 2BU3) using the Phyre2 Protein Fold Recognition Server V 2.0 on the world wide web at .sbg.bio.ic.ac.uk/-phyre2/html/page.cgi?id=index. Each mutated residue in the AtPCS1 variants identified in the yeast cadmium selection screens is indicated. Also shown is the γEC unit donated by the first GSH substrate to generate the enzyme acyl-intermediate formed in the first phase of the catalytic cycle, which was modeled from PDB: 2BU3 (25), as well as the location of the putative binding site of the second substrate, GSH (38).

FIG. 8. Variant AtPCS1 sequences of the present invention. A multiple sequence alignment of AtPCS1 and the 17 variants described in Table 1. Positions of mutations are indicated in blue. Each variant contains either single or multiple point mutations. SEQ ID NOS: 1-18 are shown.

DETAILED DESCRIPTION OF THE INVENTION

Figure 1A:
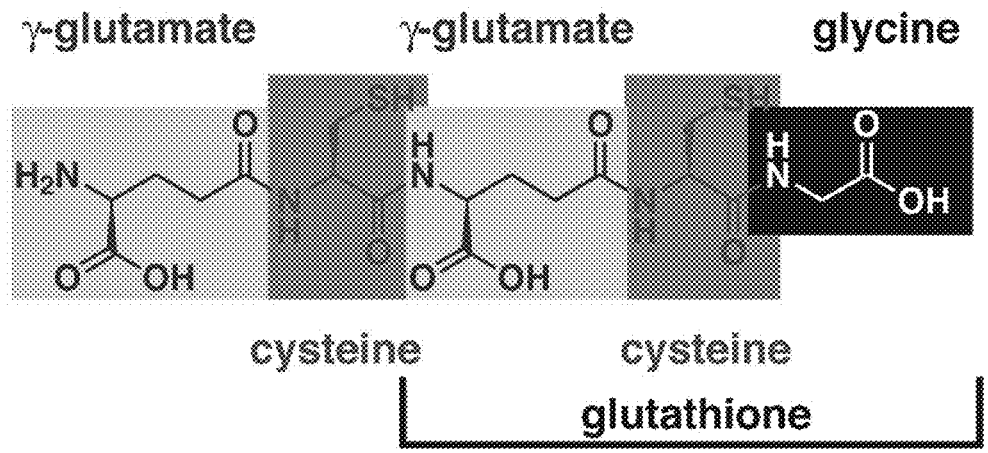
FIGS. 1A-1B. Phytochelatin structure and synthesis.
Figure 1B:
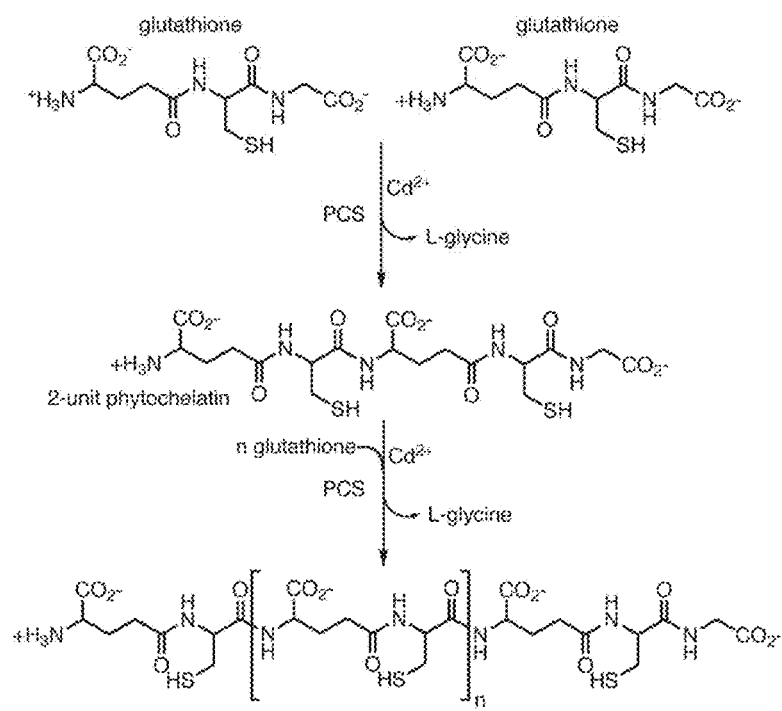

Metabolic engineering approaches are increasingly employed for environmental applications. Because phytochelatins (PC) protect plants from heavy metal toxicity, strategies directed at manipulating the biosynthesis of these peptides hold promise for the remediation of soils and groundwaters contaminated with heavy metals. Herein we describe *Arabidopsis* phytochelatin synthase (AtPCS1) mutants that confer levels of cadmium tolerance and accumulation greater than those associated with expression of the wild-type enzyme in *Saccharomyces cerevisiae, Arabidopsis* or *Brassica juncea*. Surprisingly, the AtPCS1 mutants that enhance cadmium tolerance and accumulation are catalytically less efficient than wild-type enzyme. Metabolite analyses indicate that transformation with AtPCS1, but not with the mutant variants, decreases the levels of the PC precursors, glutathione and γ-glutamylcysteine, upon exposure to cadmium. Selection of AtPCS1 variants with diminished catalytic activity alleviates depletion of these metabolites, which maintains redox homeostasis while supporting PC synthesis during cadmium exposure. These results emphasize the importance of metabolic context for pathway engineering and broaden the range of tools available for environmental remediation.

Definitions

By "phytochelatin synthase (PCS)" as used herein, is meant a protein that catalyzes the synthesis of phytochelatins. These proteins (also referred to as γ-glutamylcysteine dipeptidyl transpeptidases) synthesize PCs from GSH, homo-GSH, and related thiol peptides by transfer of a γ-glutamylcysteine unit from a thiol peptide to another or to a previously synthesized PC molecule (Rauser, 1996, Annu. Rev. Biochem. 59:61-86; Zenk, 1990, Gene 179:21-30).

"Phytochelatins," in turn, are poly-(γ-Glu-Cys)$_n$-Xaa polymers that bind heavy metals with high affinity.

By the term "nucleic acid encoding a PCS" as used herein is meant a nucleic acid encoding a polypeptide capable of producing, or which is associated with the accumulation of, phytochelatins.

The present invention includes an isolated nucleic acid encoding a biologically active polypeptide fragment of a PCS. Preferably, the isolated nucleic acid encodes a biologically active polypeptide fragment of a PCS.

As used herein, by the term "biologically active" as it refers to PCS activity as used herein, is meant a polypeptide, or a fragment thereof, which is capable of transferring a γ-glutamylcysteine unit from a thiol peptide to another or to a previously synthesized phytochelatin molecule.

Also included in the invention are isolated nucleic acids encoding biologically active variants of AtPCS1 or functional fragments thereof having a mutation listed in Table 1. Preferably, the isolated nucleic acid encoding a biologically active polypeptide fragment of a PCS is about 200 nucleotides in length. More preferably, the isolated nucleic acid encoding a biologically active polypeptide fragment of a PCS is about 400 nucleotides, even more preferably, at least about 600, yet more preferably, at least about 800, even more preferably, at least about 1000, more preferably, at least about 1200, even more preferably 1300, and yet more preferably 1400 nucleotides in length.

The invention further includes a vector comprising an isolated nucleic acid encoding a PCS and a vector comprising nucleic acid sequence encoding a biologically active fragment thereof. The procedures for the generation of a vector encoding a PCS, or fragment thereof, are well known in the art once the sequence of the gene is known, and are described, for example, in Sambrook et al., supra, Ausubel et al., supra. Suitable vectors include, but are not limited to, yeast-*E. coli* shuttle vectors as described elsewhere herein, and disarmed *Agrobacterium* tumor-inducing (Ti) plasmids (e.g., pBIN19) containing the target gene under the control of the cauliflower mosaic virus (CaMV) 35S promoter (Lagrimini et al., 1990, Plant Cell 2:7-18), its endogenous promoter or an inducible promoter (Bevan, 1984, Nucl. Acids Res. 12:8711-8721).

Further, the invention includes plant tissue-specific promoters such as are well-known in the art. These promoters direct expression of the nucleic acid operably linked thereto in certain tissue but not in others. One skilled in the art would appreciate, based upon the disclosure provided herein, that tissue-specific promoters would be useful for directing the expression of a nucleic acid encoding a PCS in a certain portion of the plant thereby localizing heavy metals to, for example, the non-harvested portion of the plant, and away from the harvested portion of the plant.

The present invention includes a method of expressing a nucleic acid encoding a PCS in one tissue of a plant but not in another using a tissue-specific promoter as discussed previously. By doing so, the present invention provides a means for accumulating toxic metals in a part of the plant which is not, for instance, harvested for human or non-human animal consumption. Thus, the invention includes a method for accumulating heavy metals in a portion of the plant, such as the leaves or roots, which is not subject to animal consumption while minimizing the level of toxic heavy metals in an edible part of the same plant.

By "harvestable portion," as the term is used herein, is meant any portion of a plant which is cultivated and gathered for human use including consumption. Such harvestable portions include, but are not limited to, the fruits, seeds, leaves, stems, and roots of various plants. Plants of interest include, without limitation, about celery, chard, kale, cauliflower, soybean, cabbage, Brussels sprouts, broccoli, and tobacco. One skilled in the art would appreciate, based on the disclosure provided herein, that the harvested portion of one plant may be the non-harvested of another. For example, the harvested portion of a cabbage plant may be the leaves but not the roots whereas the harvested portion of a potato plant for example, would be the root, or tuberous portion, but not the leaves of the plant. Further, the invention includes plants which have multiple portions which are harvested such as grape vines where both the fruits and leaves may be used for human consumption.

The "non-harvested portion" includes the portion(s) of a plant which are not used for human consumption. These parts may be used for purposes other than human or non-human animal consumption such as, but not limited to, portions of plants used for building materials. Therefore, the non-harvested portion of a plant may encompass portions which are useful and/or commercially important, but which are not used for human or non-human animal consumption, i.e., the portion is not ingested or used in food preparation.

Also included in the invention is a cell comprising an isolated nucleic acid encoding a PCS and a cell comprising an isolated nucleic acid encoding a biologically active fragment thereof.

The procedures for the generation of a cell encoding a PCS, or fragment thereof, are well known in the art once the sequence of the gene is known, and are described, for example, in Sambrook et al., supra, or Ausubel et al., 1997, supra. Suitable cells include, but are not limited to, yeast cells, bacterial cells, mammalian cells, and baculovirus-infected insect cells transformed with the gene for the express purpose of generating PCS polypeptide. In addition, plant cells transformed with the gene for the purpose of producing cells and regenerated plants having increased resistance to and increased capacity for heavy metal accumulation are included in the invention.

The invention also includes an isolated polypeptide comprising a PCS capable of producing PCs from GSH or another suitable substrate. Preferably, the isolated polypeptide comprising a PCS comprises one of the AtPCS1 variants provided in Table 1.

As used herein, the term "isolated polypeptide" describes a polypeptide which has been separated from components which naturally accompany it. Typically, a polypeptide is isolated when at least 10%, more preferably at least 20%, more preferably at least 50%, more preferably at least 60%, even more preferably at least 75%, more preferably at least 90%, and most preferably at least 99% of the total material (by volume, by wet or dry weight, or by mole percent or mole fraction) of a sample is the polypeptide of interest. The degree of isolation of the polypeptide can be measured by any appropriate method, e.g., by column chromatography, polyacrylamide gel electrophoresis, or by HPLC analysis. For example, a polypeptide is isolated when it is essentially free of naturally associated components or when it is separated from the native compounds which accompany it in its natural state.

Also included in the invention is an isolated biologically active polypeptide fragment of a PCS. Preferably, the isolated biologically active polypeptide fragment of a PCS is about 60 amino acids in length. More preferably, the isolated biologically active polypeptide fragment of a PCS is about 130 amino acids, even more preferably, at least about 200, yet more preferably, at least about 300, even more preferably, at least about 350, and more preferably, at least about 400 amino acids in length.

The invention further features an isolated nucleic acid which is in antisense orientation to a portion or all of a nucleic acid encoding a PCS comprising a variant AtPCS1 sequence, and any fragments thereof, wherein the antisense nucleic acid, or fragment thereof, is capable of inhibiting expression of the nucleic acid encoding a PCS when introduced into cells containing the nucleic acid encoding a PCS.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, through which regulatory sequences control expression of the coding sequences.

"Complementary," as used herein, refers to the nucleotide sequence complementarity between two nucleic acids, e.g., two nucleic acid molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The invention further includes a transgenic plant comprising an isolated nucleic acid encoding a variant plant PCS, or a fragment thereof, capable of producing PCs. The transgenic plant of the invention may comprise a transgene encoding a PCS polypeptide, or a fragment thereof. By "transgenic plant" as used herein, is meant a plant, the cells, the seeds and the progeny of which comprise an isolated nucleic acid inserted therein, in which the isolated nucleic acid has been manipulated to be inserted into the cells of the plant by recombinant DNA technology. The manipulated isolated nucleic acid is designated as a "transgene."

If heavy metal detoxification is limited by the rate of PC biosynthesis, transgenic plants with increased variant AtPCS1 expression would be expected to be more resistant to the toxic effects of heavy metals. By the same token, if vacuolar heavy metal sequestration is limited by the rate of PC biosynthesis, transgenic plants with increased variant AtPCS1 expression would be expected to be capable of accumulating higher vacuolar heavy metal levels than otherwise identical, non-transgenic plants. The former property permits the sustained growth of transgenic plants in the presence of heavy metal concentrations that would retard the growth of plants exhibiting normal levels of PCS expression. The latter property confers on transgenic plants the capacity for vacuolar heavy metal hyperaccumulation.

"Heavy metal resistance," as the term is used herein, means that the organism is able to tolerate a higher intracellular level of a heavy metal than an otherwise identical organism which is not heavy metal resistant. Such ability to tolerate may be demonstrated by the ability of the organism to survive and even grow and/or divide in the presence of heavy metal which would kill and/or cause an otherwise identical but non-resistant organism to not grow or divide.

Increased resistance to heavy metals has application in plant technology and plant growth in habitats polluted with xenobiotics. Since the plant vacuole frequently constitutes 40-90% of the total intracellular volume and since PCs mediate the uptake of heavy metals into this compartment, the potential for hyperaccumulation on a tissue weight basis as a result of increased production of PCs by PCS is great. Hyperaccumulators may then be used for the fixation/sequestration of heavy metals and their removal from soils.

The generation of transgenic plants comprising an isolated nucleic acid comprising the nucleic or amino acid sequence of a plant PCS, or a fragment thereof, may be accomplished by transformation of the plant with a plasmid encoding the desired nucleic acid sequence. Suitable vectors include, but are not limited to, disarmed *Agrobacterium* tumor-inducing (Ti) plasmids containing a sense or antisense strand placed under the control of the strong constitutive CaMV 35S promoter or under the control of an inducible promoter (Lagrimini et al., 1990, supra; van der Krol et al., 1988, Gene 72:45-50). Methods for the generation of such constructs, plant transformation and plant regeneration are well known in the art once the sequence of the desired gene is known and are described, for example, in Ausubel et al. (1993, Current Protocols in Molecular Biology, Greene and Wiley, New York).

Suitable vector and plant combinations will be readily apparent to those of skill in the art and can be found, for example, in Maliga et al. (1994, Methods in Plant Molecular Biology: A Laboratory Manual, Cold Spring Harbor, N.Y.).

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like.

"Expression vector" refers to a vector comprising a recombinant polynucleotide comprising expression control sequences operatively linked to a nucleotide sequence to be expressed. An expression vector comprises-sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Transformation of plants may be accomplished using the *Agrobacterium*-mediated leaf disc transformation method described by Horsch et al. (1988, Leaf Disc Transformation, Plant Molecular Biology Manual A5:1).

A number of procedures may be used to assess whether the transgenic plant comprises the desired nucleic acid. For example, genomic DNA obtained from the cells of the transgenic plant may be analyzed by Southern blot hybridization or by PCR to determine the length and orientation of any inserted, transgenic nucleic acid present therein. Northern blot hybridization analysis or PCR may be used to characterize mRNA transcribed in cells of the transgenic plant. In situations where it is expected that the cells of the transgenic plant express PCS polypeptide, or a fragment thereof, Western blot analysis may be used to identify and characterize polypeptides so expressed using antibody raised against the PCS, or fragments thereof. In situations where PCS polypeptide is expressed in a catalytically active form, PC biosynthesis assays may be used to identify and characterize the enzyme molecules so expressed. The procedures for performing such analyses are well known in the art and are described, for example, in Sambrook et al. (supra).

The transgenic plants of the invention are useful for the manipulation of heavy metal detoxification. For example, a transgenic plant encoding a variant AtPCS1 protein is useful for heavy metal detoxification when grown on soil containing heavy metals. Such plants are capable of removing heavy metals from the soil thereby generating soil which has diminished levels of compounds that are detrimental to the overall health of the environment.

Accordingly, the invention includes a method of removing heavy metals from soil comprising generating a transgenic plant having a transgene encoding a PCS and planting the plant or the seeds of the plant in the soil wherein heavy metals in the soil are hyperaccumulated/sequestered within the plant during growth of the plant in the soil. The plants are then harvested from the soil by standard agricultural methods well-known in the art or by methods to be developed in the future for harvesting of plants and/or methods developed specifically for phytoremediation.

When the levels of heavy metals in the soil have been sufficiently diminished, the transgenic plant may be removed from the soil and destroyed or discarded in an environmentally safe manner. For example, the harvested plants can be diminished in volume and/or weight by thermal, microbial, physical or chemical means to decrease handling, processing and potential subsequent land filling costs (Cunningham et al., 1996, Plant Physiol. 110:715-719). In the case of valuable metals, subsequent smelting and recovery of the metal may be cost-effective (Raskin, 1996, Proc. Natl. Acad. Sci. USA 93:3164-3166).

This technique of remediating soil is more efficient, less expensive and easier than most chemical or physical methods. The estimated costs of remediation are as follows: U.S. $10-100 per cubic meter of soil for removal of volatile or water soluble pollutants by in situ remediation using plants; U.S. $60-300 per cubic meter of soil for landfill or low temperature thermal treatment remediation of soil contaminated with the same compounds; and, U.S. $200-700 per cubic meter of soil for remediation of soil contaminated with materials requiring special landfilling arrangements or high temperature thermal treatment (Cunningham et al., 1995, Trends Biotechnol. 13:393-397).

Preferably, the transgene in the transgenic plant of the invention is a variant AtPCS1 as described in Table 1. As used herein, the term "transgene" means an exogenous nucleic acid sequence comprising a nucleic acid which encodes a promoter/regulatory sequence operably linked to nucleic acid which encodes an amino acid sequence.

By describing two polynucleotides as "operably linked" or "covalently-linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region. Covalently linked nucleic acids can produce fusion or chimeric proteins where the coding region for one polypeptide fused to another coding region for another polypeptide.

As used herein, the term "promoter/regulatory sequence" means a nucleic acid sequence which is required for expression of a gene product operably linked to the promoter/ regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

One skilled in the art, based upon the disclosure provided herein, would appreciate that expression of variant PCS in certain tissues, such as roots, may minimize the level of heavy metals present in harvestable tissues of the plant (e.g., leaves and fruits). Further, for purposes of bioremediation of contaminated groundwaters, expression of PCSs in aerial tissues would increase the accumulation of heavy metals in those tissues. Additionally, the selective expression of PCS in plant roots would enhance the ability of the plants to remove toxic heavy metals from contaminated groundwaters in a process termed "rhizofiltration." The plants containing the heavy metals could then be easily harvested from such waters thereby removing the heavy metal contaminants from groundwaters.

By "groundwater," as the term is used herein, is meant any water source, either natural or man-made.

The types of plants which are suitable for use in this method of the invention include, but are not limited to, high yield crop species for which cultivation practices have already been perfected, or engineered endemic species that thrive in the area to be remediated.

In certain situations, it may be necessary to prevent the removal of substances such as xenobiotic toxins and heavy metals from the soil or groundwater. In such situations, transgenic plants are generated comprising a transgene comprising a variant AtPCS1 or a fragment thereof, which is in the antisense orientation with respect to transcription. Such transgenes therefore serve to inhibit the function of a variant AtPCS1, in the plants thereby preventing removal of heavy metals from the soil and/or groundwater.

One skilled in the art will appreciate that one way to decrease the levels of a PCS protein in a cell is to inhibit expression of the PCS nucleic acid encoding such protein. Expression of PCS protein may be inhibited using, for example, antisense molecules, siRNA, shRNA, ribozymes, virus-induced genetic suppression, and co-suppression. Accordingly, the invention includes a method of preventing the removal of heavy metals from soil comprising generating a transgenic plant having a transgene comprising a PCS sequence which is in the antisense orientation with respect to transcription, an siRNA, shRNA or a ribozyme or a VIGS construct and/or a co-suppression construct and planting the plant or the seeds of the plant in the soil, wherein removal of heavy metals from the soil is prevented during growth of the plant in the soil.

The invention further includes an isolated nucleic acid encoding a variant PCS linked to a reporter nucleic acid. The procedures for the generation of an isolated nucleic acid encoding a PCS and a reporter nucleic acid are well known in the art once the sequence of the nucleic acid encoding PCS is known, and such techniques are described, for example, in Sambrook et al. (supra). Suitable vectors include, but are not limited to, yeast-$E.$ $coli$ shuttle vectors, disarmed $Agrobacterium$ tumor-inducing (Ti) plasmids (e.g., pBIN19) (Lagrimini et al., 1990, Plant Cell 2:7-18; Bevan, 1984, Nuci. Acids Res. 12:8711-8721).

A "reporter nucleic acid" as used herein, is one which when transcribed or translated in a cell, results in the production of a detectable product in the cell. Typically, the level of expression of the product in the cell is proportional to the activity of the promoter sequence which drives expression of the reporter nucleic acid and the nucleic acid encoding the plant PCS linked to the reporter nucleic acid. Therefore, expression of the reporter nucleic acid indicates the level of expression of the PCS and may also be used to determine the cellular location of the PCS nucleic acid and/or polypeptide expressed therefrom and linked to the reporter sequence.

Suitable reporter nucleic acids encode, for example, human influenza virus hemagglutinin (HA) epitope, the octapeptide FLAG epitope, β-glucuronidase (GUS) and green fluorescent protein (QFP), or luciferase (LUC), although any reporter nucleic acid capable of expression and detection in plant cells which are either known or heretofore unknown, may be linked to the plant PCS nucleic acids of the invention.

The present invention also includes a method of biosynthesizing a variant phytochelatin. The method comprises constructing an isolated PCS, which maintains a sufficient amount of glutathione, or a glutathione-related thiol peptide, under conditions which permit biosynthesis of phytochelatins from glutathione or other related thiol peptide.

By the term "sufficient amount," as that term is used herein, is meant an amount of glutathione, or glutathione-related thiol peptide, which allows a detectable amount of PC biosynthesis to occur under conditions which typically permit such biosynthesis.

Conditions which permit biosynthesis of phytochelatins from glutathione or other related thiol peptides are the chemical and biological parameters required for the transfer of a γ-glutamylcysteine unit from or onto a peptide. Such parameters, for example, are set forth in Grill et al. (1989, Proc. Natl. Acad. Sci. U.S.A. 89:6838-6842), and they include, but are not limited to, the presence of about 3.3 mM GSH, 10 mM 2-ME, and 200 mM Tris-HCl buffer (pH 8.0), in the absence or presence of $CdCl_2$. However, the present invention should not be construed to be limited to these or any other specific conditions for PC biosynthesis. Rather, the present invention should be construed to encompass any conditions under which a detectable level of enzymatic transfer of a γ-glutamylcysteine unit from a substrate onto another molecule may take place in the presence of any required ions, substrates and/or cofactors.

By "glutathione-related thiol peptide," as the term is used herein, is meant any peptide which may be used by a PCS to transfer a γ-glutamylcysteine unit from that peptide onto another moiety or onto which a PCS may transfer a γ-glutamylcysteine unit from another source. Such GSH-related thiol peptides include, but are not limited to, homoglutathione, $PC_2$, $PC_3$, and $PC_4$.

"Biosynthesis," as the term is used herein, means any bona fide catalytic reaction mediated by an enzyme to produce a compound. In one embodiment, the biosynthesis is the enzymatic reaction whereby an isolated PCS produces a phytochelatin by transfer of a γ-glutamylcysteine unit from GSH to another related thiol peptide. However, the present invention encompasses PC biosynthesis performed in vitro in an appropriate buffer system in the presence of purified PCS, GSH, or any other related thiol peptide source of γ-glutamylcysteine units, and a concentration of heavy metal ion sufficient to activate PCS-mediated PC biosynthesis as disclosed elsewhere herein. Purified PCS may be employed at a concentration ranging from about 0.1 μs to about 0.1 mg/ml, GSH {or, for example, γ-glutamylcysteine, $PC_2$, $PC_3$, or $PC_4$, or homo-GSH, hydroxymethyl-GSH (γ-Glu-Cys-Ser), or γ-glutamylcysteinylglutamic acid (Zenk et al., supra)} at a concentration ranging from about 0.1 μM to about 50 mM, and heavy metal (e.g., $Cd^{2+}$, $Hg^{2+}$, $Pb^{2+}$, $As^{3+}$, $Cu^{2+}$, $Ni^{2+}$, or $Zn^{2+}$) at a concentration ranging from about 0.1 to about 500 μM. Thus, PC biosynthesis requires at least a PCS (e.g., AtPCS1, AtPCS2, TaPCS1, SpPCS, or CePCS), GSH (as γ-glutamylcysteine donor or acceptor), and a heavy metal activator. The invention should not be construed to be limited to biosynthesis of any particular phytochelatin or to reactions where the γ-glutamylcysteine unit is derived from GSH; rather, the present invention should be construed to encompass the synthesis of any (γ-Glu-Cys)$_n$ polymer mediated by a PCS molecule.

Further, the present invention is intended to encompass biosynthesis of variant PCs whether in vitro using PCS from biological extracts as well as biosynthesis performed in vivo. In one embodiment, the biosynthesis is performed by heterologous expression of a variant AtPCS1 in yeast cells.

The present invention encompasses PC biosynthesis performed in vitro in an appropriate buffer system in the presence of a purified PCS, GSH, or any other related thiol peptide source of γ-glutamylcysteine units, and an amount of $CdCl_2$ sufficient to elicit PCS-catalyzed biosynthesis of PCs as disclosed herein.

The following materials and methods are provided to facilitate the practice of the present invention. They are not intended to limit the invention in any way.

Materials.

*Saccharomyces cerevisiae* ycf1Δ strain DTY167 (MAT Δ ura3-52 leu2-3, -112 his-Δ 200 trp1-Δ 901 lys2-801 suc2-Δ 9 ycf1::hisG) which is $Cd^{2+}$-hypersensitive (27-28), pYES3 yeast-*Escherichia coli* expression vector (29), which is a derivative of pYES2 (Invitrogen) with the galactose-inducible promoter replaced by the constitutive 3-phosphoglycerate kinase promoter and engineered to encode a C-terminal FLAG epitope tag, and the pYES3-AtPCS1::FLAG vector (11) were used for the mutant screens and analyses of the effects of constitutively heterologously expressed AtPCS1. The pART27 vector (30) was provided by Dr. Edgar Cahoon. *Arabidopsis thaliana* ecotype Col-0 and *Brassica juncea* seeds (accession no. 173874) were obtained from the *Arabidopsis* Biological Research Center (Ohio State University, Columbus, Ohio) and the North Central Regional Plant Introduction Station (Ames, Iowa), respectively. The pET28a-AtPCS1 construct was previously described (26). For the generation of pET28a-AtPCS1-mutant constructs, AtPCS1 coding regions were PCR-amplified from the appropriate vectors and subcloned into pET28a.

Mutant Library Generation and Screens.

Random mutagenesis of AtPCS1 (GenBank: AF085230) was performed directly on the pYES3-AtPCS1::FLAG construct (11) using the GeneMorph kit (Stratagene). Reactions were performed using template quantities estimated to give 1-4 base pair changes per gene copy. The gel-purified PCR amplification products were ligated into NotI/BamH1 double-digested pYES3 to generate an expression construct library. After transformation by electroporation into *E. coli* DH5α for amplification, plasmid DNA was isolated and transformed into *S. cerevisiae* ycf1 Δ DTY167 cells using a Frozen EZ II yeast transformation kit (Zymo Research). The library of transformants was amplified by growth at 30° C. on CSM/ura⁻ medium supplemented with 0.17% yeast nitrogen base without amino acids, 0.5% ammonium sulfate, and 2% dextrose. To screen for $Cd^{2+}$ tolerant Ura⁺ transformants, the library was plated on media supplemented with 0-1 mM $CdCl_2$.

Generation and Preliminary Characterization of Transgenic Plants.

For *Arabidopsis* transformation, the wild-type and mutant AtPCS1::FLAG inserts from pYES3 were subcloned into pART27 (30), a modified binary vector with a cauliflower mosaic virus 35S promoter-driven expression cassette and a kanamycin-resistance marker. The pART27, pART27-AtPCS1::FLAG, and pART27-AtPCS1-Y186C::FLAG vectors were introduced into *Agrobacterium tumefaciens* by electroporation, and *Arabidopsis* plants were transformed by the floral dip method and grown to maturity. After selecting and harvesting the T1 seeds, multiple kanamycin-resistant lines were isolated for the generation of T2 seeds. T2 seeds exhibiting a 3:1 segregation ratio on kanamycin plates were used for the subsequent isolation of multiple independent homozygous lines whose identity was confirmed by PCR. To confirm expression of FLAG-tagged AtPCS1, the seedlings were ground in liquid nitrogen and extracted in 50 mM potassium phosphate buffer (pH 8). Proteins were separated by SDS-PAGE and electrotransferred to nitrocellulose membranes for western analysis with anti-FLAG M2 antibody (Sigma-Aldrich). Immunoreactive bands were visualized by enhanced chemiluminescence (Amersham). An in vitro plant tissue culture method was used to transform *B. juncea* (31-32). The pART27, pART27-AtPCS1::FLAG, and pART27-AtPCS1-Y186C::FLAG vectors were transformed into *Agrobacterium* and 200-300 *B. juncea* hypocotyl segments each for the vector control, AtPCS1, and AtPCS-Y186C constructs were subjected to transformation. Stable kanamycin-resistant transformants were identified by PCR and used to generate T2 seeds for subsequent analysis. Expression of FLAG-tagged AtPCS1 was confirmed by western analysis as described for the *Arabidopsis* transformants.

Yeast Heavy Metal Tolerance Assays.

To assess the capacity of heterologously expressed wild-type and mutant AtPCS1::FLAG for conferring heavy metal tolerance, *S. cerevisiae* ycf1.4 strain DTY167 was transformed with pYES3 vector, pYES3 containing AtPCS1::FLAG insert, or pYES3 containing mutant AtPCS1::FLAG insert and grown at 30° C. to an $A_{600\ nm}$ of 1.5-1.8 in AHC medium supplemented with glucose and tryptophan before inoculating aliquots into 4-mL of the same medium containing the concentrations of $CdCl_2$ indicated. After growth for 12-24 h, when the subcultures were in mid-logarithmic phase, the concentrations of $Cd^{2+}$ required to cause a 50% diminution of cell density ($IC_{50}$) were estimated spectrophotometrically (11).

Measurement of PCs, γEC, and GSH.

The cellular PC contents of yeast transformed with pYES3, wild-type pYES3-AtPCS1::FLAG or mutant pYES3-AtPCS1::FLAG were estimated as described previously (11) by reversed-phase HPLC and spectrophotometric measurements of the thiol content of the chromatographic fractions after reaction with Ellman's reagent (5,5'-dithiobis(nitrobenzoic acid)) at $A_{412\ nm}$. The PC contents of plant materials were estimated after the addition of 300 µL of 1 M NaOH containing 1 µg µL⁻¹ $NaBH_4$ to 100 µL aliquots of the tissue homogenates and centrifugation of the samples for 3 min at 13,000×g. Reversed-phase HPLC of the supernatants from centrifugation was performed on a Hypersil ODS $C_{18}$ column (250×4.6 mm; 5 µm particle size) after acidification of the samples with 5% 5-sulfosalicylic acid. The column was developed with a 0-20% linear concentration gradient of acetonitrile/0.1% formic acid at a flow rate of 0.5 mL min⁻¹ and the thiol contents of the chromatographic fractions were estimated spectrophotometrically after reaction with Ellman's reagent as described above. The γEC and total glutathione contents of yeast and plant extracts were estimated fluorimetrically after derivatization of the samples with monobromobimane as described previously (33). Levels of free glutathione (GSH) and glutathione disulfide (GSSG) were determined using glutathione reductase and 2-vinylpyridine (34).

Mass Spectrometry.

The identities of the PCs isolated from extracts of the $Cd^{2+}$-grown yeast DTY167 pYES3-AtPCS1::FLAG transformants, which were subsequently used as standards for their identification in plant extracts, were confirmed by matrix-assisted laser desorption ionization time-of-flight (MALDI-TOF) mass spectrometry (MS). Samples (1 µL) of the HPLC-purified PC fractions were mixed with 10 µL of matrix solution (10 mg mL⁻¹ α-cyano-4-hydroxycinnamic acid in 0.1% trifluoroacetic acid/acetonitrile+water (1:1)) and applied to a MALDI plate for laser desorption ionization and detection in negative ion mode in a Voyager-DE STR system (Applied Biosystems). The PCs identified in the yeast extracts (with their monoisotopic [M-H]⁻ m/z values in parenthesis) were $PC_2$ (−538.82), $PC_3$ (−769.31), $PC_4$ (−1001.89) and $PC_5$ (−1232.67).

Estimation of Cadmium Content of Yeast and Plant Extracts.

The $Cd^{2+}$ contents of yeast strain DTY167 after transformation with pYES3, pYES3-AtPCS1::FLAG or mutant pYES3-AtPCS1::FLAG were estimated after growth at 30° C. for 24 h in media containing 0, 5, 50 or 250 µM $CdCl_2$. The cultures were pelleted by centrifugation and washed twice with 1.5 mM tartaric acid for 15 min before lyophilization. After weighing, the dry lyophilizates were exhaustively digested with 65% nitric acid at 200° C. for 6 h for metal analysis. For measurements of the $Cd^{2+}$ content of plant tissues, stable transformants were selected by germination on Murashige-Skoog (MS) agar plates containing kanamycin (30 µM) before the transfer of seedlings to plates containing 0 and 100 µM $CdCl_2$ and growth for three weeks. After harvesting, the shoots of the seedlings were thoroughly washed with deionized water, dried at 70° C. for 48 h, weighed and digested in a mixture of nitric and perchloric acid (7:1). Sample digests were analyzed using a Perkin-Elmer AAnalyst 300 atomic absorption spectrometer.

Measurement of PCS Activity.

Wild-type and mutant AtPCS1 were overexpressed and purified from E. coli BL21(DE3) for determination of enzymatic activity and kinetic parameters (26). Unless indicated to the contrary, the PCS activities of affinity-purified N-terminally His-tagged wild-type and mutant AtPCS1 were assayed in media containing 3.3 mM GSH, 50 µM $CdCl_2$ and 100 mM BTP-HEPES buffer, pH 8.0 at 30° C. for 10 min as described (23). For the quantitation of PCs, thiols were estimated spectrophotometrically in the RP-HPLC-separated fractions after reaction with 5,5'-dithio-bis(2-nitrobenzoic acid). Rates of PC synthesis were expressed as thiols (micromole) incorporated per min per mg protein (µmol $min^{-1}$ mg $protein^{-1}$).

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example I

Mutations in the N-Terminal Catalytic Domain of AtPCS1 Increase Heavy Metal Tolerance Random mutagenic PCR was employed to generate a library of AtPCS1 variants that were subcloned into the yeast-E. coli shuttle vector pYES3 for constitutive heterologous expression in the $Cd^{2+}$-hypersensitive ycf1Δ S. cerevisiae strain DTY167. All AtPCS1 variants were C-terminally FLAG-tagged to facilitate immunodetection. DNA sequencing of 200 randomly selected clones from a total pool of ~30,000 randomly mutagenized pYES3-AtPCS1::FLAG constructs established that mutations were distributed throughout the coding sequence of AtPCS1. To identify AtPCS1::FLAG mutants that conferred improved $Cd^{2+}$ tolerance compared to wild-type AtPCS1::FLAG, yeast strain DTY167 transformed with empty pYES3 vector or vector containing either wild-type or mutant AtPCS1::FLAG was plated on agar plates containing 0-1 mM $CdCl_2$. Although the majority of yeast transformants containing either wild-type or mutant pYES3-AtPCS1::FLAG grew on plates with 0 to 200 µM $Cd^{2+}$, there was a subset of transformants capable of growing on plates containing up to 800 µM $Cd^{2+}$. Sequence analysis of the pYES3-AtPCS1::FLAG constructs isolated from the colonies growing on plates containing 800 µM $CdCl_2$ identified 17 variants containing 1-4 amino acid substitutions largely in the N-terminal catalytic domain (residues 1-221) of the enzyme (Table 1).

TABLE 1

Summary of AtPCS1 mutants that enhance $Cd^{2+}$ tolerance when heterologously expressed in S. cerevisiae ycf1Δ strain DTY167.

| AtPCS1 variant | $IC_{50}$ (mM)[a] | $PC_2$-$PC_5$ content (nmol mg $protein^{-1}$)[b] | Specific activity (µmol $min^{-1}$ mg $protein^{-1}$)[c] |
|---|---|---|---|
| Wild-type | 0.15 ± 0.05 | 9 ± 1 | 16.8 ± 1.4 |
| Q48R/C144Y/G168S/W280R | 0.55 ± 0.14 | 26 ± 6 | 5.0 ± 0.4 |
| S51T/N143I/N170I/H220R | 0.71 ± 0.13 | 38 ± 8 | 3.3 ± 0.5 |
| E52K | 0.82 ± 0.18 | 32 ± 4 | 3.2 ± 0.4 |
| A59V | 0.73 ± 0.10 | 34 ± 8 | 2.9 ± 0.8 |
| S60C/S202I | 0.58 ± 0.09 | 30 ± 9 | 5.9 ± 0.3 |
| D71N | 0.68 ± 0.14 | 35 ± 7 | 5.1 ± 0.3 |
| R74H/S230C/L250R | 0.71 ± 0.15 | 40 ± 8 | 3.7 ± 0.6 |
| F83C/N170D | 0.81 ± 0.27 | 35 ± 9 | 3.1 ± 0.7 |
| C91S/A199S | 0.69 ± 0.19 | 25 ± 5 | 4.6 ± 0.4 |
| V97L | 0.64 ± 0.13 | 25 ± 9 | 4.8 ± 0.5 |
| V97C | 0.81 ± 0.16 | 44 ± 9 | 2.8 ± 0.1 |
| C109Y | 1.02 ± 0.18 | 50 ± 4 | 1.8 ± 0.3 |
| T123R/F163I | 0.70 ± 0.19 | 36 ± 7 | 3.6 ± 0.3 |
| T139P | 0.72 ± 0.15 | 37 ± 4 | 2.6 ± 0.9 |
| V181G | 0.76 ± 0.10 | 33 ± 3 | 2.8 ± 0.1 |
| A182G/A282V/G329S | 0.66 ± 0.15 | 28 ± 8 | 5.5 ± 0.7 |
| Y186C | 1.18 ± 0.12 | 56 ± 9 | 1.3 ± 0.2 |

[a]$IC_{50}$ values for yeast heterologously expressing AtPCS1 variants were determined in liquid medium (11).
[b]PC content, expressed as the sum total of $PC_{2-5}$ was determined by RP-HPLC (11).
[c]Specific activities of AtPCS1 variants were determined after purification of their His-tagged derivatives from E. coli (11, 26).
Values shown are means ± SE (n = 3).

Enhanced $Cd^{2+}$ Tolerance and Increased PC Accumulation in Yeast Expressing Mutant AtPCS1.

Figure 2A:
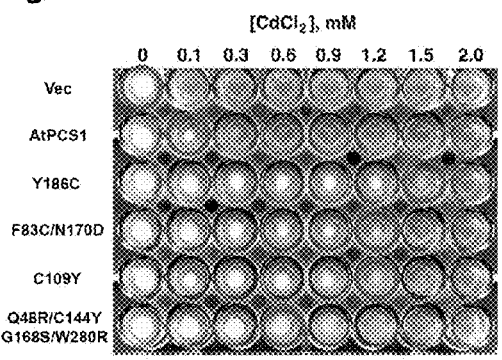
FIGS. 2A-2D. $Cd^{2+}$ tolerance, PC accumulation, and $Cd^{2+}$ accumulation in yeast strain DTY167 heterologously expressing wild-type or mutant variants of AtPCS1::FLAG.
Figure 2B:
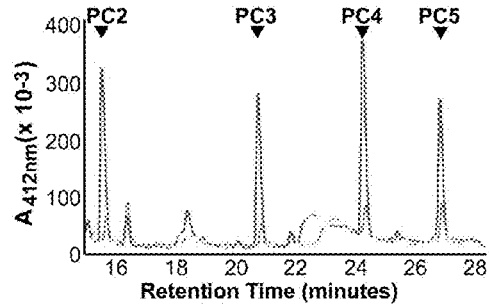
Figure 2C:
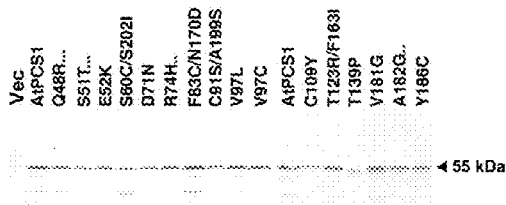
Figure 3:
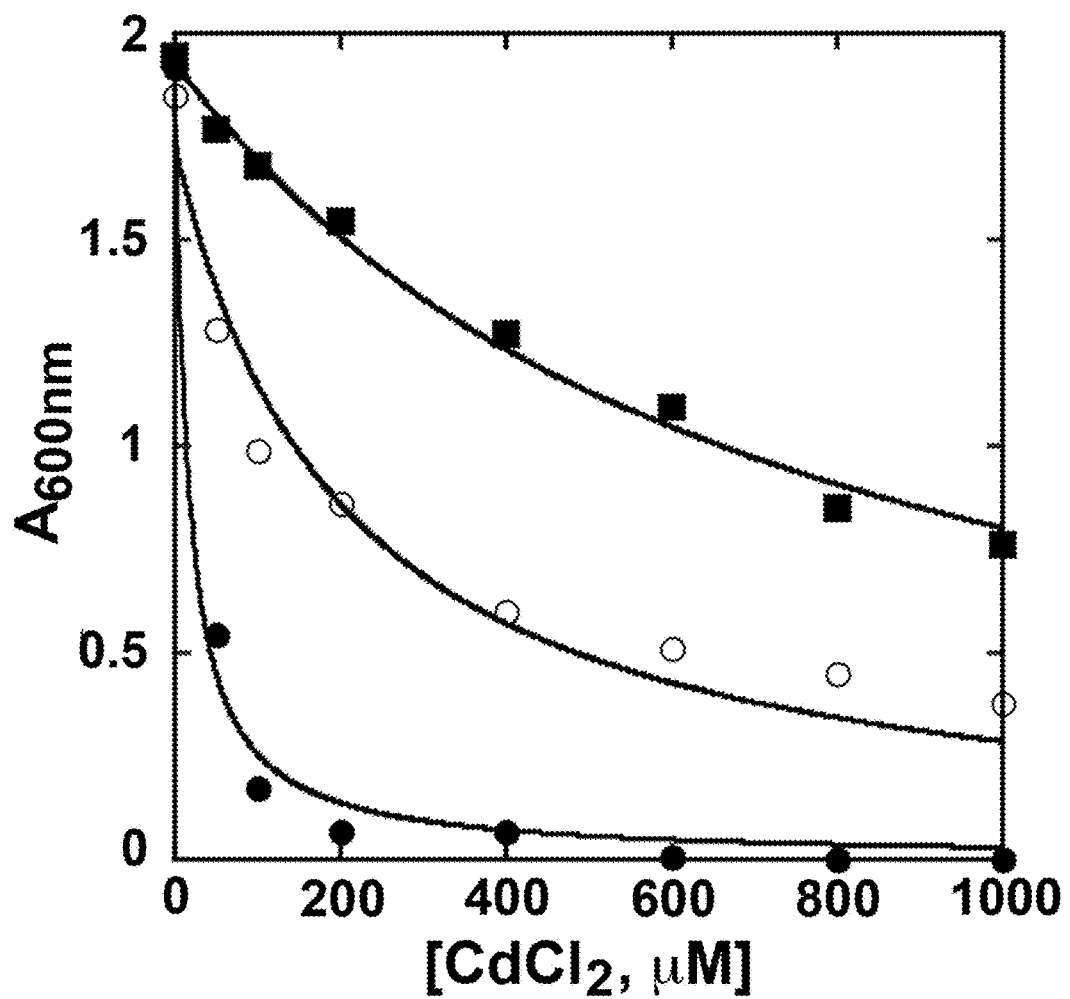
FIG. 3. Effect of heterologously expressed wild-type and mutant AtPCS1 on the $Cd^{2+}$ sensitivity of S. cerevisiae ycf1Δ strain DTY167. Yeast strain DTY167 was transformed with empty pYES3 vector (closed circles) or with pYES3 containing either the AtPCS1::FLAG insert (pYES3-AtPCS1::FLAG; open circles) or the mutant AtPCS1-Y186C::FLAG insert (pYES3-AtPCS1-Y186C::FLAG; closed squares). $Cd^{2+}$ sensitivity was assessed in liquid media containing the indicated concentrations of $CdCl_2$ as described.

For characterization of the mutants isolated from the screen that conferred enhanced $Cd^{2+}$ tolerance, individual clones were re-transformed into DTY167 cells and assayed for cadmium tolerance on agar plates (FIG. 2A) and in liquid media (FIG. 3; Table 1). Transformants of strain DTY167 expressing the AtPCS1 mutants displayed 4- to 8-fold increases in $Cd^{2+}$ tolerance compared to transformants expressing wild-type AtPCS1 based on the concentration of $CdCl_2$ required to decrease cell density by 50% ($IC_{50}$) after growth for 24 h. Each mutant not only increased $Cd^{2+}$ tolerance but also $Cd^{2+}$-elicited PC accumulation by 3- to 6-fold compared to wild-type (FIG. 2B; Table 1). In agreement with previous studies (11), the principal PCs synthesized after exposure of the transformants to $Cd^{2+}$ were $PC_2$, $PC_3$, $PC_4$ and $PC_5$ (FIG. 2B), as confirmed by reversed-phase high-performance liquid chromatography (RP-HPLC) and matrix-assisted laser desorption time-of-flight mass spectrometry (MALDI-TOF MS). In no case were PCs detectable in the pYES3 control cells, plus or minus $Cd^{2+}$, or in any of the pYES3-AtPCS1::FLAG transformants grown in media devoid of $Cd^{2+}$. The increases in $Cd^{2+}$ tolerance and cellular PC content associated with heterologous expression of mutant AtPCS1 in yeast were, with one exception, not attributable to an increase in the amount, stability, or integrity of the protein. Sixteen of the 17 mutant lines contained levels of the FLAG-tagged $M_r$ 55,000 polypeptide comparable to yeast expressing wild-type AtPCS1 (FIG. 2C). The one exception was the AtPCS1-F83C/N170D double mutant, which showed a slight increase in the level of FLAG-tagged protein (FIG. 2C).

Increased $Cd^{2+}$ Accumulation in Yeast Expressing Mutant AtPCS1.

Figure 2D:
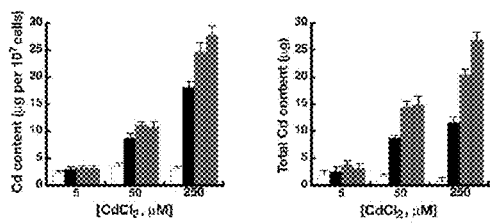

A key determinant of the utility of engineered PCS variants is that enhanced tolerance and PC production are accompanied by increased heavy metal accumulation. With this in mind, AtPCS1-C109Y and AtPCS1-Y186C, the two AtPCS1 mutants identified in the yeast screens that conferred the highest levels of $Cd^{2+}$ tolerance and cellular PC accumulation (Table 1), were chosen for investigations of their effects on metal accumulation. The cellular $Cd^{2+}$ contents of yeast strains transformed with pYES3 vector, pYES3-AtPCS1::FLAG, pYES3-AtPCS1-C109Y::FLAG, and pYES-AtPCS1-Y186C::FLAG were determined after growth for 24 h in liquid media containing 5, 50 or 250 µM $CdCl_2$. Yeast heterologously expressing either mutant established cellular $Cd^{2+}$ contents greater than those achieved with empty vector or by overexpression of wild-type enzyme (FIG. 2D). Expression of AtPCS1::FLAG increased $Cd^{2+}$ accumulation on a per cell basis versus vector controls, but the enhancements associated with the expression of AtPCS1-C109Y::FLAG and AtPCS1-Y186C::FLAG were 1.3- to 1.8-fold greater at 250 µM $Cd^{2+}$ (FIG. 2D). Indeed, when cellular $Cd^{2+}$ accumulation was normalized on the basis of total cell weight rather than cell number, the differences were even more pronounced. The total cellular $Cd^{2+}$ accumulation in media containing 250 µM $CdCl_2$ was 2- to 3-fold higher in cultures of AtPCS1-C109Y::FLAG and AtPCS1-Y186C::FLAG transformants than cultures of AtPCS1::FLAG transformants (FIG. 2D). This increase in total $Cd^{2+}$ content reflects the enhanced accumulation per cell in combination with the greater cell densities achieved by the AtPCS1-C109Y::FLAG and AtPCS1-Y186C::FLAG transformants compared to the wild-type AtPCS1::FLAG transformants.

Ectopic Expression of Wild-Type AtPCS1 and AtPCS1-Y186C in *Arabidopsis*.

Figure 4A:
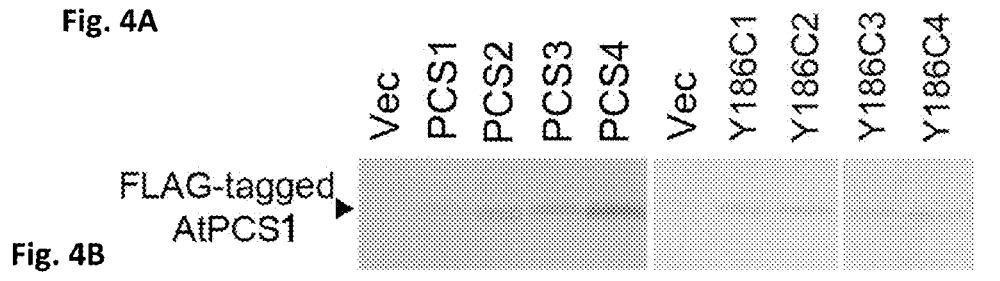
FIGS. 4A-4D. Effects of ectopic expression of AtPCS1::FLAG or AtPCS1-Y186C::FLAG in Arabidopsis on $Cd^{2+}$ tolerance, PC accumulation, and $Cd^{2+}$ accumulation.

To Test whether ectopic expression of an AtPCS1 variant would improve cadmium tolerance and/or accumulation in plants, we compared the effect of AtPCS1 and AtPCS-Y186C overexpression in *Arabidopsis*. Multiple lines of *Arabidopsis* transformed with the empty pART27 vector, pART27-AtPCS1::FLAG, or pART27-AtPCS1-Y186C::FLAG were generated. One T2 line of the pART27 transformants and four independent T2 lines each of the pART27-AtPCS1::FLAG (lines PCS1-4) and pART27-AtPCS1-Y186C::FLAG transformants (lines Y186C1-4) were studied further. After confirming expression of FLAG-tagged wild-type and mutant AtPCS1 in the transformants by western analysis (FIG. 4A), seeds were germinated on standard horizontal MS plates before transfer of the seedlings to vertical MS plates containing 0-200 µM $CdCl_2$ to assess tolerance in terms of the effects of $Cd^{2+}$ on root growth.

Figure 4B:
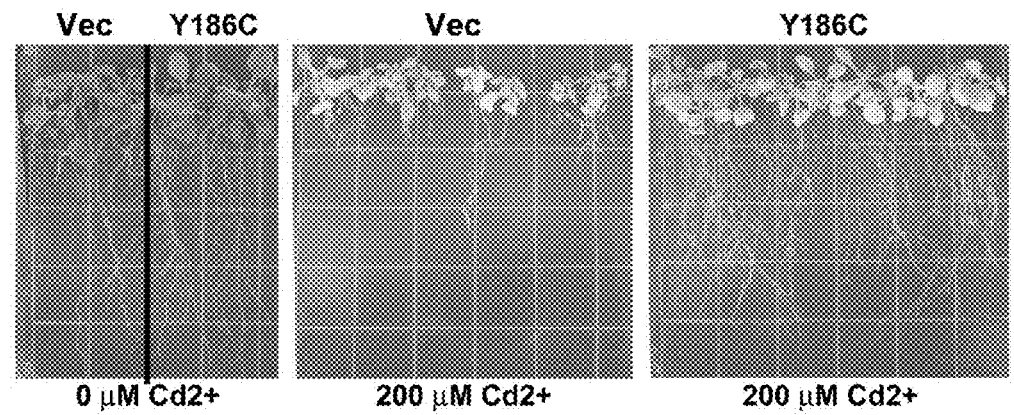
Figure 4C:
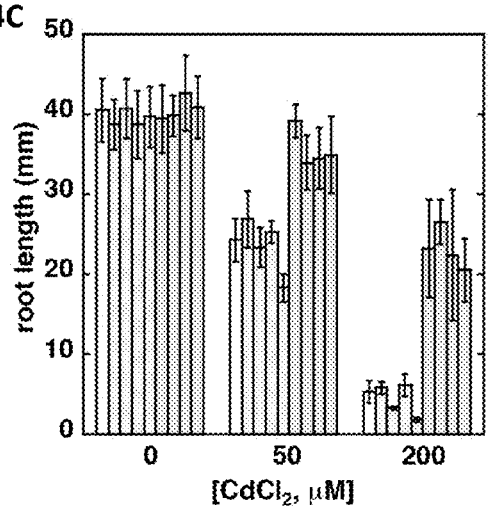
Figure 4D:
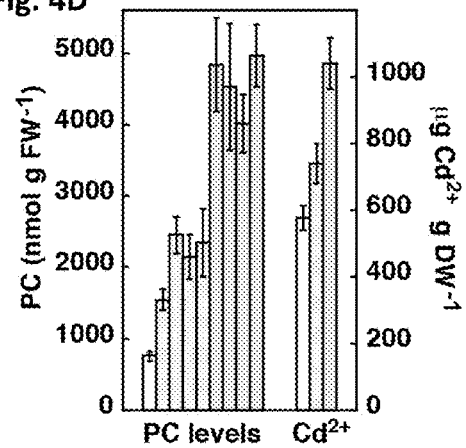

As described by others (35-36), overexpression of AtPCS1 in *Arabidopsis* yielded seedlings that showed little no change in $Cd^{2+}$ tolerance as determined from root growth assays compared to the pART27 controls. In contrast, overexpression of AtPCS1-Y186C::FLAG improved $Cd^{2+}$ tolerance (FIG. 4B). All four lines expressing AtPCS1-Y186C::FLAG showed increased $Cd^{2+}$ tolerance (FIG. 4C), as indicated by an up to 6-fold increase in root length over that of pART27 controls or pART27-AtPCS1::FLAG transformants after 10 d growth on plates containing 200 µM $CdCl_2$ (FIG. 4C). Analysis of the tissue PC levels of the seedlings after 10 d growth on plates containing 100 µM $CdCl_2$ revealed a 2- to 3-fold increase in pART27-AtPCS1::FLAG transformants and up to a 6-fold increase in pART27-AtPCS1-Y186C::FLAG transformants versus pART27 controls (FIG. 4D). Expression of AtPCS1-Y186C approximately doubled the levels of $Cd^{2+}$ in seedlings after 10 d growth on plates containing 100 µM $CdCl_2$ by comparison with controls, and elicited a 1.3-fold increase by comparison with pART27-AtPCS1::FLAG transformants (FIG. 4D).

Ectopic Expression of Wild-Type AtPCS1 and AtPCS1-Y186C in *B. juncea*.

Figure 5A:
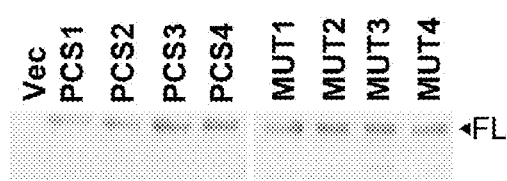
FIGS. 5A-5E. Effects of AtPCS1::FLAG or AtPCS1-Y186C::FLAG expression in B. juncea on $Cd^{2+}$ tolerance, PC accumulation and $Cd^{2+}$ accumulation.
Figure 5B:
Figure 5C:
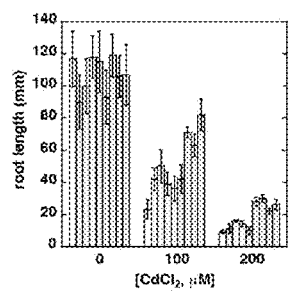
Figure 5D:
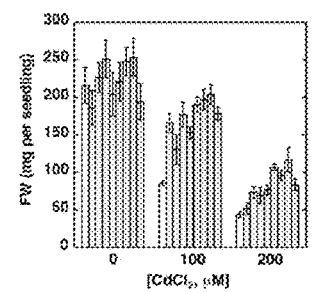
Figure 5E:
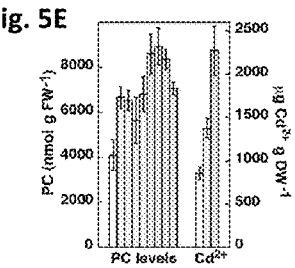

The encouraging results obtained from *Arabidopsis* ectopically expressing mutant AtPCS1, and knowing that the variable results obtained using wild-type PCS clones in this plant species apply also to *Nicotiana tabacum* (tobacco) and *B. juncea* (Indian mustard) (31-32; 37-39), prompted expansion of the studies described here to another plant species to gauge the general applicability of our findings. As a fast growing genetically manipulatable plant of greater biomass than *Arabidopsis* and with a high intrinsic capacity for trace metal accumulation (38-40), *B. juncea*, which for these reasons lends itself to heavy metal remediation, was the species of choice. Transgenic *B. juncea* lines for AtPCS1::FLAG and the AtPCS1-Y186C::FLAG mutant were generated by hypocotyl transformation and tissue culture. After confirming expression of FLAG-tagged protein in four lines each of the AtPCS1::FLAG and AtPCS1-Y186C::FLAG transformants by western analysis (FIG. 5A), they were subjected to $Cd^{2+}$ tolerance screens in parallel with measurements of PC and $Cd^{2+}$ accumulation. As determined for *Arabidopsis*, ectopic expression of AtPCS1::FLAG and AtPCS1-Y186C::FLAG resulted in pronounced differences in $Cd^{2+}$ tolerance, PC accumulation, and $Cd^{2+}$ accumulation (FIG. 5B-E). Whereas expression of AtPCS1::FLAG conferred modest (<2-fold) increases in $Cd^{2+}$ tolerance, PC accumulation, and $Cd^{2+}$ accumulation compared to untransformed seedlings, expression of AtPCS1-Y186C::FLAG enhanced these three attributes by 4-, 2- and 3-fold, respectively, compared to untransformed controls (FIG. 5C-E).

Association Between Enhanced $Cd^{2+}$ Tolerance and Decreased Catalytic Efficiency.

Figure 6A:
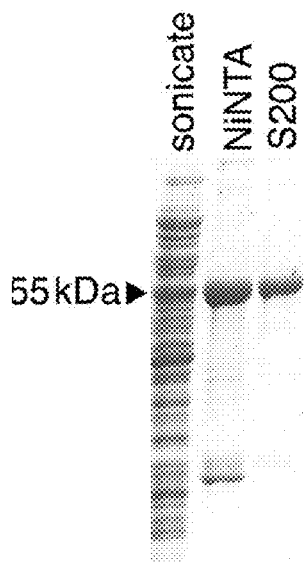
FIGS. 6A-6C. Purification, kinetic analysis, and homology modeling of AtPCS1.
Figure 6B:
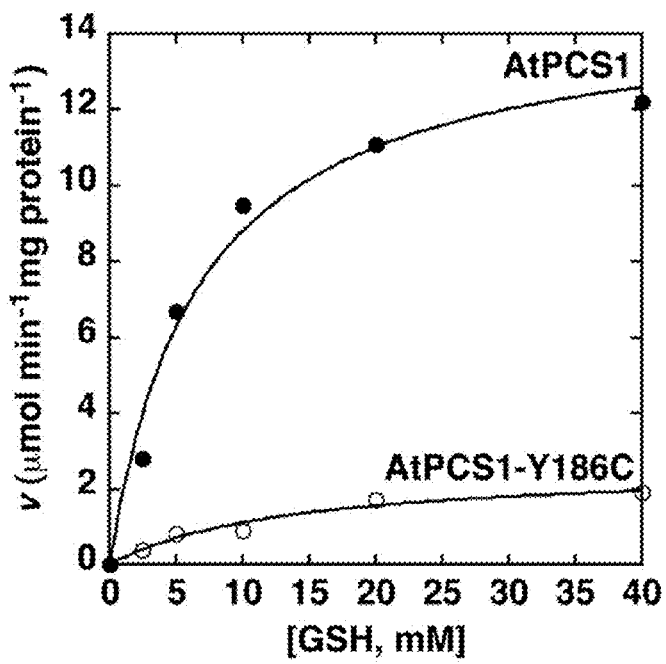

In identifying AtPCS1 variants with amino acid substitutions that map to the N-terminal catalytic domain, our expectation was that the mutations would improve catalytic efficiency, when in fact the contrary was found. All 17 of the AtPCS1 variants that enhanced $Cd^{2+}$ tolerance and accumulation had 3- to 13-fold lower specific activities compared to wild-type enzyme (FIG. 6A; Table 1). Whereas the specific activity of AtPCS1 (16.8 μmol $min^{-1}$ mg $protein^{-1}$) was comparable to those obtained in previous studies (26), the activities of the AtPCS1 mutants ranged from 1.3 to 5.9 μmol mg $protein^{-1}$ (Table 1). In the specific case of AtPCS1-Y186C, which was kinetically characterized in detail because it conferred the greatest improvement in the AtPCS1-dependent $Cd^{2+}$ tolerant phenotype in yeast, Arabidopsis and B. juncea, the diminished activity was associated with a decrease in $V_{max}$ (from 14.7 to 2.1 μmol $min^{-1}$ mg $protein^{-1}$) and an increase in $K_m^{GSH}$ (from 6.7 to 16.4 mM) versus wild-type to give an overall 17-fold decrease in catalytic efficiency (FIG. 6B). No differences between the PC product profiles or the kinetics of activation by $Cd^{2+}$ of AtPCS1 and AtPCS1-Y186C were discernible.

Maintenance of Upstream PC Precursor Levels.

In S. cerevisiae, Arabidopsis, and B. juncea, overexpression of the kinetically less efficient AtPCS1-Y186C mutant led to higher levels of PCs, improved $Cd^{2+}$ tolerance, and enhanced $Cd^{2+}$ accumulation compared to expression of wild-type enzyme. Based on our observations, we speculated that the AtPCS1-Y186C mutant maintains PC synthesis without imposing a drain on cellular GSH and γEC levels and/or changes in the ratio of reduced to oxidized glutathione (GSH/GSSG ratio). To explore this possibility we examined the levels of GSH and γEC and the GSH/GSSG ratio before and after exposure to $Cd^{2+}$ in yeast and plants expressing either AtPCS1 or AtPCS1-Y186C (Table 2). In all three of the organisms engineered for heterologous or ectopic expression, the same pattern was seen.

AtPCS1 when heterologously expressed in yeast or ectopically overexpressed in Arabidopsis or B. juncea was associated with a decrease in the levels of total glutathione and γEC and changes in the GSH/GSSG ratio following exposure to 200 μM $CdCl_2$. The decreases in GSH and γEC after $Cd^{2+}$ exposure versus controls ranged from about 5% to as much as 40-50% depending on the metabolite and/or organism (Table 2). For example, in yeast overexpressing AtPCS1, the pre-treatment levels of GSH and GSSG were 6,026 and 404 nmol $g^{-1}$ DW, respectively. Following $Cd^{2+}$ exposure, the total glutathione pool is diminished by ~20% and the levels of GSH and GSSG were 3,914 and 1,186 nmol $g^{-1}$ DW, respectively. In contrast, expression of AtPCS1-Y186C in each organism generally maintained the levels of total glutathione and γEC and the GSH/GSSG ratio (Table 2).

TABLE 2

Effect of $Cd^{2+}$ on thiol metabolites in yeast, Arabidopsis, and B. juncea transformed with wild-type and mutant AtPCS1.

| | Control | | AtPCS1 | | AtPCS1-Y186C | |
|---|---|---|---|---|---|---|
| | +0 μM $CdCl_2$ | +200 μM $CdCl_2$ | +0 μM $CdCl_2$ | +200 μM $CdCl_2$ | +0 μM $CdCl_2$ | +200 μM $CdCl_2$ |
| Yeast | | | | | | |
| γEC | 53 ± 14 | 74 ± 16 | 42 ± 4 | 45 ± 6 | 65 ± 3 | 54 ± 5 |
| total glutathione | 6,800 ± 430 | 5,280 ± 680 | 6,430 ± 110 | 5,100 ± 170 | 6,230 ± 290 | 7,980 ± 620 |
| GSH/GSSG ratio | 16.4 ± 2.6 | 5.1 ± 1.4 | 14.9 ± 3.5 | 3.3 ± 0.8 | 16.9 ± 2.4 | 15.5 ± 2.9 |
| Arabidopsis | | | | | | |
| γEC | 20 ± 7 | 17 ± 10 | 17 ± 9 | 10 ± 5 | 25 ± 2 | 19 ± 6 |
| total glutathione | 845 ± 93 | 751 ± 47 | 820 ± 12 | 684 ± 58 | 862 ± 100 | 989 ± 74 |
| GSH/GSSG ratio | 7.3 ± 1.2 | 1.4 ± 0.6 | 7.5 ± 2.3 | 2.8 ± 0.5 | 7.4 ± 1.6 | 5.9 ± 1.5 |
| B. juncea | | | | | | |
| γEC | 14 ± 8 | 122 ± 18 | 11 ± 3 | 138 ± 15 | 16 ± 7 | 167 ± 63 |
| total glutathione | 930 ± 160 | 1,155 ± 120 | 920 ± 160 | 730 ± 67 | 965 ± 49 | 1,080 ± 90 |
| GSH/GSSG ratio | 10.5 ± 1.9 | 2.9 ± 0.5 | 11.8 ± 1.4 | 3.8 ± 1.9 | 10.7 ± 1.0 | 9.5 ± 1.4 |

Yeast, Arabidopsis, and B. juncea transformed with empty vector (control) or vector containing either AtPCS1 or AtPCS1-Y186C inserts were grown in 0 and 200 μM $CdCl_2$ for determination of γEC and total glutathione levels and GSH/GSSG ratio (42-43). For Arabidopsis, lines PCS3 and Y186C1 were used; for B. juncea, lines PCS2 and Y186C4 were used. Values shown are nmol $g^{-1}$ DW for yeast and nmol $g^{-1}$ FW for plants and are means ± SE (n = 3).

Discussion

Figure 8:
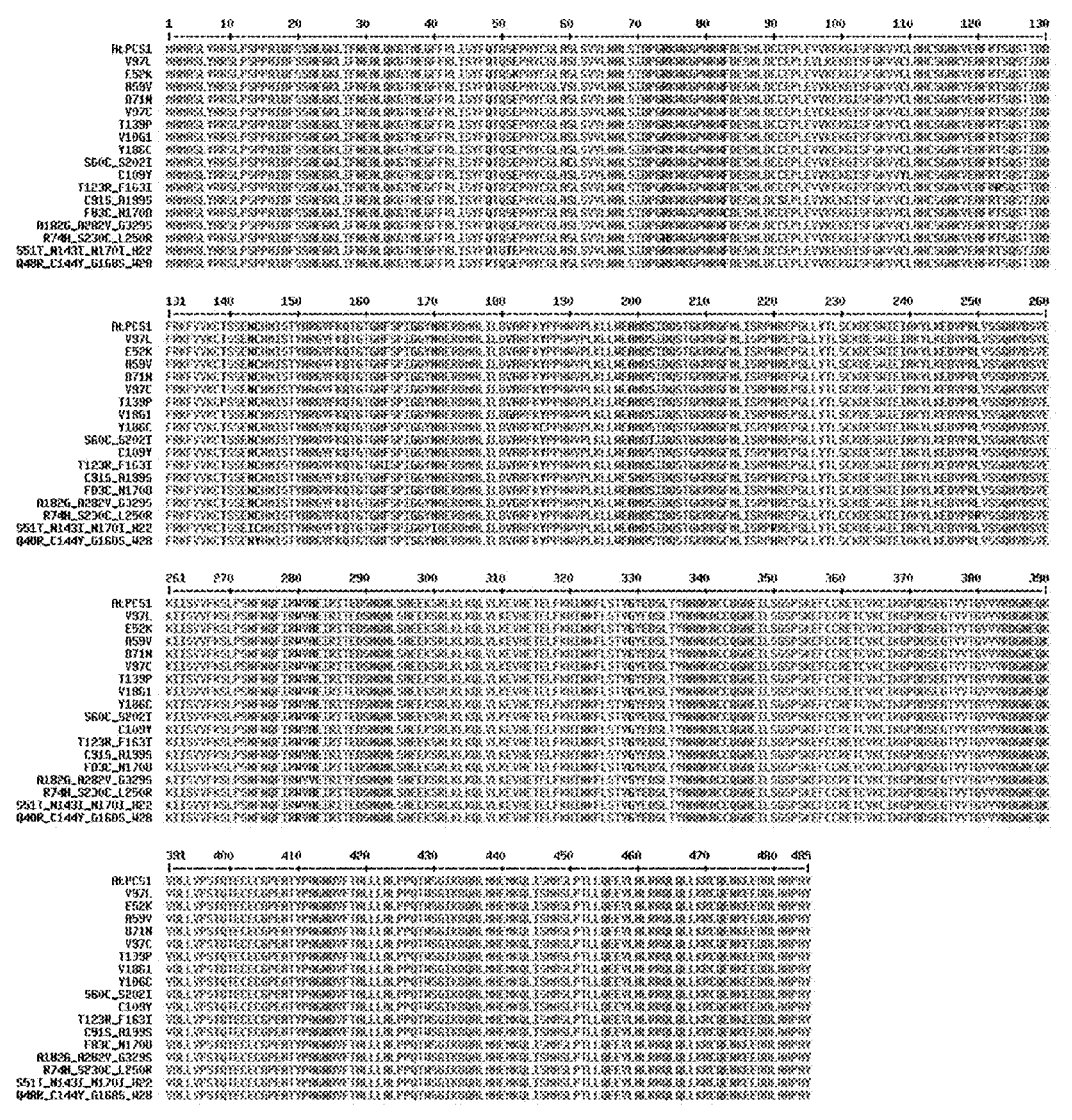

Directed evolution and protein engineering strategies aim to improve the biochemical function of a protein. Typically, for an enzyme, the enhancement of catalytic efficiency for a new substrate or alteration in physiochemical properties, such as thermostability, lead to new functionality and applications. To improve the ability of PCS to protect yeast and plants against heavy metal toxicity, the use of random mutagenesis and screening for $Cd^{2+}$ tolerance led to the identification of mutants with the desired phenotype in multiple organisms (FIGS. 2-5); however, the biochemical properties of the AtPCS1 mutants were all inferior to the wild-type enzyme (Table 1 and FIG. 8). The adaptive engineering of AtPCS1 provides an example of how a metabolic system can constrain biochemical function for an improved biological outcome.

In a variety of organisms, PCS plays a critical role in providing a basal level of protection against a range of heavy metals (10-18, 22-26). Comparison of the PCS from different species shows that the N-terminal catalytic domain is more similar among all the homologs (~50% identity), than the C-terminal domain, which is highly variable both in sequence and amino acid length (22). Three lines of evidence support a catalytic role for the N-terminal domain. First, limited proteolysis demonstrates that the N-terminal domain of AtPCS1 is sufficient for PC synthesis (24, 26). Second, Cys56 is acylated by γEC during the reaction that extends the length of the PC chain and is an essential catalytic residue (26). Third, the identification of a protein from the cyanobacterium *Nostoc*, which is similar in sequence to the N-terminal domain of AtPCS1, catalyzes the hydrolysis of glycine from GSH (25). The specific role of the variable C-terminal region of the PCS in different organisms remains unclear.

Figure 6C:
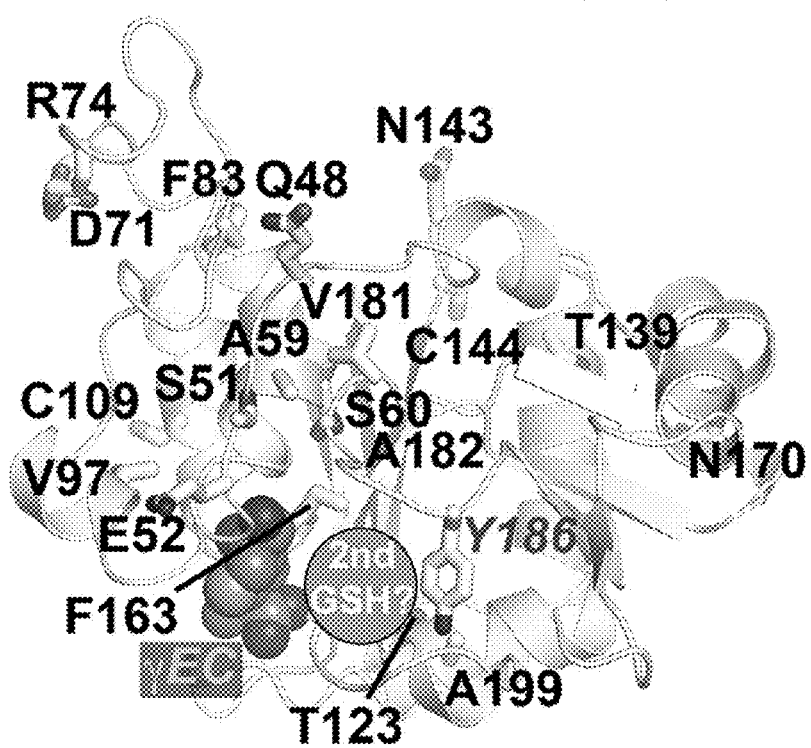

Because of the domain architecture of AtPCS1, it is notable that of the 31 point mutations in the AtPCS1 variants isolated from the $Cd^{2+}$ tolerance screen, 26 were in the N-terminal catalytic domain (Table 1; FIG. 6C). Random sequencing of the original random mutagenesis library showed a distribution of mutations across the length of the coding region; however, the pool of mutants isolated after selection for $Cd^{2+}$ tolerance clearly implicates the N-terminal catalytic domain as a key feature for the improved phenotype.

Homology modeling of the catalytic domain of AtPCS1 based on the structure of the GSH hydrolase from *Nostoc* (25) (FIG. 6C) suggests that many of the amino acid substitutions identified in the screen localize to putative substrate interaction loops (Ser51, Glu52, Ala59, Ser60, Phe163, Ala182, Tyr186) and secondary structural features proximal to the active site (Val97, Cys109, Thr123, Val181, Ala199) (25, 41). For instance, recent structure-function studies and modeling of AtPCS1 indicates that Y186 on loop B of the structure forms part of the binding site for the second substrate (41), which is probably GSH (17, 26) (FIG. 6C). This may explain why the impaired catalytic activity of AtPCS1-Y186C was associated with an increased $K_m^{GSH}$ concomitant with a decrease in $V_{max}$ with little or no change in the susceptibility of the enzyme to activation by $Cd^{2+}$.

Knowing that the inherent reactivity of heavy metals toward thiol groups is not only a major factor in their toxicity but is also crucial for their detoxification by GSH through the removal of reactive active oxygen species, high-level ectopic expression of fully active AtPCS1 may impose conflicting demands on GSH and its immediate precursor γEC for alleviating oxidative stress associated with heavy metal toxicity (17, 38-39). Consistent with this notion is the fact that while constitutive endogenous expression of PCS provides a basic level of protection against heavy metal toxicity (FIG. 7, black), as loss of PCS activity leads to sensitivity to a variety of heavy metals (11-15, 23) the activity of this enzyme is tightly regulated. Although PCS is expressed in plants (and fission yeast such as *Schizosaccaromyces pombe*), enzymatic activity is only detected in the presence of heavy metals (11-13; 16-18). Moreover, sequestration of heavy metals by either PC or other chelating agents terminates PCS activity both in vitro and in vivo (42).

Figure 7:
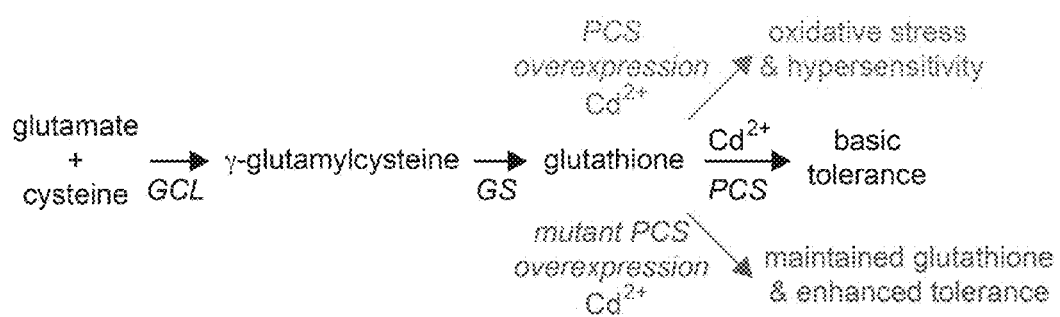
FIG. 7. Model for adaptive evolution of PC biosynthesis before and after transformation with wild-type or mutant PCS. GSH biosynthesis catalyzed by glutamate-cysteine ligase (GCL) and glutathione synthetase (GS) provides substrates for PCS. Heavy metal activation of PCS elicits the synthesis of PCs and basal level tolerance (black). Overexpression of wild-type PCS leads to oxidative stress through the depletion of GSH and/or γEC and heavy metal hypersensitivity in some plants (orange). Overexpression of mutant PCS variants with diminished enzymatic activity, but with wild-type heavy metal activation, maintains GSH and γEC levels and enhances heavy metal tolerance (green).

Overexpression of fully active AtPCS1 leads to enzymatic activation following metal exposure, which promotes PC synthesis from GSH (FIG. 7, orange). The higher levels of PCS begin to make PC from GSH, which can contribute to heavy metal detoxification; however, if the pathways supplying the substrate do not maintain metabolite levels in the presence of highly expressed and fully activated PCS, this exacerbates oxidative stress through consumption of cellular GSH and γEC reserves and changes in the GSH/GSSG ratio (Table 2). Because cellular redox potential is highly sensitive to small changes in both the GSH/GSSG ratio and total glutathione levels (43), this can lead to oxidative stress conditions. In fact, this is the molecular basis for the effect of buthionine sulfoximine, an inhibitor of γ-glutamylcysteine ligase, on rapidly growing tumor cells and for its effects on plant glutathione biosynthesis (44-47).

In contrast, analysis of GSH and γEC levels and the GSH/GSSG ratio in yeast, *Arabidopsis*, and *B. juncea* (Table 2) indicate that overexpression of the less active AtPCS1-Y186C maintains the reservoir of these metabolites following $Cd^{2+}$ exposure (FIG. 7, green). These results underscore the importance of cellular redox state for supporting metabolism linked to heavy metal tolerance. As suggested here, maintaining both total glutathione levels and the ratio of reduced:oxidized peptide is important for providing substrates for PCS but also for the activation of other enzymes in plant sulfur metabolism that support glutathione production (45-56). Similar to earlier work showing that either lower-level expression of AtPCS1 or supplementation of the growth medium with exogenous GSH alleviates $Cd^{2+}$ hypersensitivity (38-39), the selection of lower activity PCS variants appears to strike a balance between maintaining redox buffering capacity of cellular GSH and supporting sustained PC production, which leads to improved $Cd^{2+}$ tolerance and enhanced $Cd^{2+}$ accumulation. Moreover, the effect of overexpressing less active PCS variants suggests that tuning of wild-type protein expression could be another useful approach to modulate metal tolerance in different organisms. In addition, coupling of PC production with modifications in the vacuolar transporter that remove the chelated metals from the cell can also be performed (57-62).

Ultimately, efforts to engineer different components of heavy metal detoxification systems in plants at the protein and pathway level offer tools for environmental remediation. Although directed evolution aims to improve proteins and pathways for optimized biochemical properties and/or biological phenotypes (3), our results emphasize the importance of the metabolic context of the target protein for engineering. Considering the connection of PCs to the major cellular redox buffer, GSH, our counterintuitive finding—kinetic inferiority leading to phenotypic superiority—demonstrates the need to approach metabolic engineering with a systems-level perspective to identify key control points amenable to the adaptive and context-dependent engineering of plant and microbial metabolism.

REFERENCES

1. Johnson M D, Kenney N, Stoica A, Hilakivi-Clarke L, Singh B, Chepko G, Clarke R, Sholler P F, Lirio A A, Foss C, Reiter R, Trock B, Paik S, & Martin M B (2003) Cadmium mimics the in vivo effects of estrogen in the uterus and mammary gland. *Nature Med.* 9: 1081-1084.
2. Salt D E, Smith R D, & Raskin I (1998) Phytoremediation. *Annu. Rev. Plant Physiol. Plant Mol. Biol.* 49: 643-668.
3. Lassner M & Bedbrook J (2001) Directed molecular evolution in plant improvement. *Curr. Opin. Plant Biol.* 4: 152-156.

4. Rugh C L, Wilde H D, Stack N M, Thompson D M, Summers A O, & Meagher R B (1996) Mercuric ion reduction and resistance in transgenic *Arabidopsis thaliana* plants expressing a modified bacterial merA gene. *Proc. Natl. Acad. Sci. USA* 93: 3182-3187.
5. Bizily S P, Rugh C L, & Meagher R B (2000) Phytodetoxification of hazardous organomercurials by genetically engineered plants. *Nature Biotech.* 18: 213-217.
6. Dhankher O P, Li Y, Rosen B P, Shi J, Salt D, Senecoff J F, Sashti N A, & Meagher R B (2002) Engineering tolerance and hyperaccumulation of arsenic in plants by combining arsenate reductase and gamma-glutamylcysteine synthetase expression. *Nature Biotech.* 20: 1140-1145.
7. Song W Y, Sohn E J, Martinoia E, Lee Y J, Yang Y Y, Jasinski M, Forestier C, Hwang I, & Lee Y (2003) Engineering tolerance and accumulation of lead and cadmium in transgenic plants. *Nature Biotech.* 21: 914-919.
8. Jez J M (2011) Toward protein engineering for phytoremediation: possibilities and challenges. *Int. J. Phytoremediation* 12: S77-89.
9. Clemens S, Aarts M G, Thomine S, Verbruggen N (2013) Plant science: the key to preventing slow cadmium poisoning. *Trends Plant Sci.* 18: 92-99.
10. Cobbett C & Goldsbrough P (2002) Phytochelatins and metallothioneins: roles in heavy metal detoxification and homeostasis. *Annu. Rev. Plant Biol.* 53: 159-182.
11. Vatamaniuk O K, Mari S, Lu Y P, & Rea P A (1999) AtPCS1, a phytochelatin synthase from *Arabidopsis*: isolation and in vitro reconstitution. *Proc. Natl. Acad. Sci. USA* 96: 7110-7115.
12. Ha S B, Smith A P, Howden R, Dietrich W M, Bugg S, O'Connell M J, Goldsbrough P B, & Cobbett C S (1999) Phytochelatin synthase genes from *Arabidopsis* and the yeast *Schizosaccharomyces pombe*. *Plant Cell* 11: 1153-1164.
13. Clemens S, Kim E J, Neumann D, & Schroeder J I (1999) Tolerance to toxic metals by a gene family of phytochelatin synthases from plants and yeast. *EMBO J.* 18: 3325-3333.
14. Howden R, Goldsbrough P B, Andersen C R, & Cobbett C S (1995) Cadmium-sensitive, cad1 mutants of *Arabidopsis thaliana* are phytochelatin deficient. *Plant Physiol.* 107: 1059-1066.
15. Howden R, Andersen C R, Goldsbrough P B, & Cobbett C S (1995) A cadmium-sensitive, glutathione-deficient mutant of *Arabidopsis thaliana*. *Plant Physiol.* 107: 1067-1073.
16. Rea P A (2012) Phytochelatin synthase: of a protease a peptide polymerase made. *Physiol. Plant.* 145: 154-164.
17. Vatamaniuk O K, Mari S, Lu Y P, & Rea P A (2000) Mechanism of heavy metal ion activation of phytochelatin (P C) synthase: blocked thiols are sufficient for P C synthase-catalyzed transpeptidation of glutathione and related thiol peptides. *J. Biol. Chem.* 275: 31451-31459.
18. Vatamaniuk O K, Mari S, Lang A, Chalasani S, Demkiv L O, & Rea P A (2004) Phytochelatin synthase, a dipeptidyltransferase that undergoes multisite acylation with gamma-glutamylcysteine during catalysis: stoichiometric and site-directed mutagenic analysis of *Arabidopsis thaliana* PCS1-catalyzed phytochelatin synthesis. *J. Biol. Chem.* 279: 22449-22460.
19. Mendoza-Cózatl D G, Zhai Z, Jobe T O, Akmakjian G Z, Song W Y, Limbo O, Russell M R, Kozlovskyy V I, Martinoia E, Vatamaniuk O K, Russell P, & Schroeder J I (2010) Tonoplast-localized Abc2 transporter mediates phytochelatin accumulation in vacuoles and confers cadmium tolerance. *J. Biol. Chem.* 285: 40416-40426.
20. Song W Y, Park J, Mendoza-Cózatl D G, Suter-Grotemeyer M, Shim D, Hortensteiner S, Geisler M, Weder B, Rea P A, Rentsch D, Schroeder J I, Lee Y, Martinoia E (2010) Arsenic tolerance in *Arabidopsis* is mediated by two ABCC-type phytochelatin transporters. *Proc. Natl. Acad. Sci. USA* 107: 21187-21192.
21. Park J, Song W Y, Ko D, Eom Y, Hansen T H, Schiller M, Lee T G, Martinoia E, Lee Y (2012) The phytochelatin transporters AtABCC1 and AtABCC2 mediate tolerance to cadmium and mercury. *Plant J.* 69: 278-288.
22. Rea P A, Vatamaniuk O K, & Rigden D J (2004) Weeds, worms, and more: papain's long-lost cousin, phytochelatin synthase. *Plant Physiol.* 136: 2463-2474.
23. Vatamaniuk O K, Bucher E A, Ward J T, & Rea P A (2001) A new pathway for heavy metal detoxification in animals: phytochelatin synthase is required for cadmium tolerance in *Caenorhabditis elegans*. *J. Biol. Chem.* 276: 20817-20820.
24. Ruotolo R, Peracchi A, Bolchi A, Infusini G, Amoresano A, & Ottonello S (2004) Domain organization of phytochelatin synthase: functional properties of truncated enzyme species identified by limited proteolysis. *J. Biol. Chem.* 279: 14686-14693.
25. Vivares D, Arnoux P, & Pignol D (2005) A papain-like enzyme at work: native and acyl-enzyme intermediate structures in phytochelatin synthesis. *Proc. Natl. Acad. Sci. USA* 102: 18848-18853.
26. Romanyuk N D, Rigden D J, Vatamaniuk O K, Lang A, Cahoon R E, Jez J M, Rea P A (2006) Mutagenic definition of a papain-like catalytic triad, sufficiency of the N-terminal domain for single-site core catalytic enzyme acylation, and C-terminal domain for augmentative metal activation of a eukaryotic phytochelatin synthase. *Plant Physiol.* 141: 858-869.
27. Lu Y P, Li Z S, & Rea P A (1997) AtMRP1 gene of *Arabidopsis* encodes a glutathione S-conjugate pump: isolation and functional definition of a plant ATP-binding cassette transporter gene. *Proc. Natl. Acad. Sci. USA* 94: 8243-8248.
28. Li Z S, Lu Y P, Zhen R G, Szczypka M, Thiele D J, & Rea P A (1997). A new pathway for vacuolar cadmium sequestration in *Saccharomyces cerevisiae*: YCF1-catalyzed transport of bis(glutathionato)cadmium. *Proc. Natl. Acad. Sci. USA* 94: 42-47.
29. Li Z S, Szczypka M, Lu Y P, Thiele D J, & Rea P A (1996) The yeast cadmium factor protein (YCF1) is a vacuolar glutathione S-conjugate pump. *J. Biol. Chem.* 271: 6509-6517.
30. Gleave A P (1992) A versatile binary vector system with a T-DNA organisational structure conducive to efficient integration of cloned DNA into the plant genome. *Plant Mol. Biol.* 20: 1203-1207.
31. Zhu Y, Pilon-Smits E A, Jouanin L, & Terry N (1999) Overexpression of glutathione synthetase in indian mustard enhances cadmium accumulation and tolerance. *Plant Physiol.* 119: 73-80.
32. Zhu Y L, Pilon-Smits E A, Tarun A S, Weber S U, Jouanin L, & Terry N (1999) Cadmium tolerance and accumulation in Indian mustard is enhanced by overexpressing gamma-glutamylcysteine synthetase. *Plant Physiol.* 121: 1169-1178.
33. Cameron J C & Pakrasi H B (2010) Essential role of glutathione in acclimation to environmental and redox perturbations in the cyanobacterium *Synechocystis* sp. PCC 6803. *Plant Physiol.* 154: 1672-1685.

34. Griffith O W (1980) Determination of glutathione and glutathione disulfide using glutathione reductase and 2-vinylpyridine. *Anal. Biochem.* 106: 207-212.
35. Lee S, Moon J S, Ko T S, Petros D, Goldsbrough P B, & Korban S S (2003) Overexpression of *Arabidopsis* phytochelatin synthase paradoxically leads to hypersensitivity to cadmium stress. *Plant Physiol.* 131: 656-663.
36. Li Y, Dhankher O P, Carreira L, Lee D, Chen A, Schroeder J I, Balish R S, & Meagher R B (2004) Overexpression of phytochelatin synthase in *Arabidopsis* leads to enhanced arsenic tolerance and cadmium hypersensitivity. *Plant Cell Physiol.* 45: 1787-1797.
37. Pomponi M, Censi V, Di Girolamo V, De Paolis A, di Toppi L S, Aromolo R, Costantino P, & Cardarelli M (2006) Overexpression of *Arabidopsis* phytochelatin synthase in tobacco plants enhances Cd(2+) tolerance and accumulation but not translocation to the shoot. *Planta* 223: 180-190.
38. Gasic K & Korban S S (2007) Transgenic Indian mustard (*Brassica juncea*) plants expressing an *Arabidopsis* phytochelatin synthase (AtPCS1) exhibit enhanced As and Cd tolerance. *Plant Mol. Biol.* 64: 361-369.
39. Gasic K & Korban S S (2007) Expression of *Arabidopsis* phytochelatin synthase in Indian mustard (*Brassica juncea*) plants enhances tolerance for Cd and Zn. *Planta* 225: 1277-1285.
40. Pilon-Smits EAH & Pilon M (2002) Phytoremediation of metals using transgenic plants. *Crit. Rev. Plant Sci.* 21: 439-456.
41. Chia J C, Yang C C, Sui Y T, Lin S Y, & Juang R H (2013) Tentative identification of the second substrate binding site in *Arabidopsis* phytochelatin synthase. *PLoS One* 8: e82675.
42. Loeffler S, Hochberger A, Grill E, Winnacker E L, Zenk M H (1989) Termination of the phytochelatin synthase reaction through sequestration of heavy metals by the reaction product. *FEBS Lett.* 258: 42-46.
43. Winterbourn C C (2008) Reconciling the chemistry and biology of reactive oxygen species. *Nature Chem. Biol.* 4: 278-286.
44. Meister A (1995) Glutathione biosynthesis and its inhibition. *Methods Enzymol.* 252: 26-30.
45. Jez J M, Cahoon R E, Chen S (2004) *Arabidopsis thaliana* glutamate-cysteine ligase: functional properties, kinetic mechanism, and regulation of activity. *J. Biol. Chem.* 279: 33463-33470.
46. Jez J M, Cahoon R E (2004) Kinetic mechanism of glutathione synthetase from *Arabidopsis thaliana. J. Biol. Chem.* 279: 42726-42731.
47. Hicks L M, Cahoon R E, Bonner E R, Rivard R S, Sheffield J, Jez J M (2007) Thiol-based regulation of redox-active glutamate-cysteine ligase from *Arabidopsis thaliana. Plant Cell* 19: 2653-2661.
48. Bick J A, Setterdahl A T, Knaff D B, Chen Y, Pitcher L H, Zilinskas B A, Leustek T (2001) Regulation of the plant-type 5'-adenylyl sulfate reductase by oxidative stress. *Biochemistry* 40: 9040-9048.
49. Hothorn M, Wachter A, Gromes R, Stuwe T, Rausch T, Scheffzek K (2006) Structural basis for the redox control of plant glutamate cysteine ligase. *J. Biol. Chem.* 281: 27557-27665.
50. Gromes R, Hothorn M, Lenherr E D, Rybin V, Scheffzek K, Rausch T (2008) The redox switch of gamma-glutamylcysteine ligase via a reversible monomer-dimer transition is a mechanism unique to plants. *Plant J.* 54: 1063-1075.
51. Yi H, Galant A, Ravilious G E, Preuss M L, Jez J M (2010) Sensing sulfur conditions: simple to complex protein regulatory mechanisms in plant thiol metabolism. *Mol. Plant* 3: 269-279.
52. Ravilious G E, Nguyen A, Francois J A, Jez J M (2012) Structural basis and evolution of redox regulation in plant adenosine-5'-phosphosulfate kinase. *Proc. Natl. Acad. Sci. USA* 109: 309-314.
53. Zhang M, Ravilious G E, Hicks L M, Jez J M, McCulla R D (2012) Redox switching of adenosine-5'-phosphosulfate kinase with photoactivatable atomic oxygen precursors. *J. Am. Chem. Soc.* 134: 16979-16982.
54. Ravilious G E, Jez J M (2012) Structural biology of plant sulfur metabolism: from assimilation to biosynthesis. *Nat. Prod. Rep.* 29: 1138-1152.
55. Ravilious G E, Jez J M (2012) Nucleotide binding site communication in *Arabidopsis thaliana* adenosine 5'-phosphosulfate kinase. *J. Biol. Chem.* 287: 30385-30394.
56. Ravilious G E, Westfall C S, Jez J M (2013) Redox-linked gating of nucleotide binding by the N-terminal domain of adenosine 5'-phosphosulfate kinase. *J. Biol. Chem.* 288: 6107-6115.
57. Vatamaniuk O K, Bucher E A, Sundaram M V, Rea P A (2005) CeHMT-1, a putative phytochelatin transporter, is required for cadmium tolerance in *Caenorhabditis elegans. J. Biol. Chem.* 280: 23684-23690.
58. Mendoza-Cozatl D G, Zhai Z, Jobe T O, Akmakjian G Z, Song W Y, Limbo O, Russell M R, Kozlovskyy V I, Martinoia E, Vatamaniuk O K, Russell P, Schroeder J I (2010) Tonoplast-localized Abc2 transporter mediates phytochelatin accumulation in vacuoles and confers cadmium tolerance. *J. Biol. Chem.* 285: 40416-40426.
59. Song W Y, Park J, Mendoza-Cozatl D G, Suter-Grotemeyer M, Shim D, Hortensteiner S, Geisler M, Weder B, Rea P A, Rentsch D, Schroeder J I, Lee Y, Martinoia E (2010) Arsenic tolerance in *Arabidopsis* is mediated by two ABCC-type phytochelatin transporters. *Proc. Natl. Acad. Sci. USA* 107: 21187-21192.
60. Park J, Song W Y, Ko D, Eom Y, Hansen T H, Schiller M, Lee T G, Martinoia E, Lee Y (2012) The phytochelatin transporters AtABCC1 and AtABCC2 mediate tolerance to cadmium and mercury. *Plant J.* 69: 278-288.
61. Huang J, Zhang Y, Peng J S, Zhong C, Yi H Y, Ow D W, Gong J M (2012) Fission yeast HMT1 lowers seed cadmium through phytochelatin-dependent vacuolar sequestration in *Arabidopsis. Plant Physiol.* 158: 1779-1788.
62. Brunetti P, Zanella L, De Paolis A, Di Litta D, Cecchetti V, Falasca G, Barbieri M, Altamura M M, Costantino P, Cardarelli M (2015) Cadmium-inducible expression of the ABC-type transporter AtABCC3 increases phytochelatin-mediated cadmium tolerance in *Arabidopsis. J. Exp. Bot.* 66: 3815-3829.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid encoding a variant phytochelatin synthase (PCS), wherein the synthase exhibits diminished catalytic activity relative to native, wild type synthase, wherein said PCS variant has one or more amino acid substitutions selected from
   Q48R/C144Y/G168S/W280R (SEQ ID NO: 18);
   S51T/N143I/N170I/H220R (SEQ ID NO: 17);
   E52K (SEQ ID NO: 3);
   A59V (SEQ ID NO: 4);
   S60C/S202I (SEQ ID NO: 10);
   D71N (SEQ ID NO: 5);
   R74H/S230C/L250R (SEQ ID NO: 16);
   F83C/N170D (SEQ ID NO: 14);
   C91S/A199S (SEQ ID NO: 13);
   V97L (SEQ ID NO: 2);
   V97C (SEQ ID NO: 6);
   C109Y(SEQ ID NO: 11);
   T123R/F163I (SEQ ID NO: 12);
   T139P (SEQ ID NO: 7);
   V181G (SEQ ID NO: 8);
   A182G/A282V/G329S (SEQ ID NO: 15); and
   Y186C (SEQ ID NO: 9).

2. The isolated nucleic acid encoding the PCS of claim 1, wherein said variant comprises a Y186C (SEQ ID NO: 9) substitution.

3. An isolated nucleic acid encoding a plant PCS of claim 1, wherein said variant comprises a C109Y (SEQ ID NO: 11) substitution.

4. The isolated nucleic acid of claim 1, wherein the nucleic acid further comprises a reporter nucleic acid covalently linked thereto.

5. The isolated nucleic acid of claim 4, said reporter nucleic acid encoding a reporter polypeptide selected from the group consisting of a FLAG octapeptide, a human influenza virus hemagglutinin epitope, a β-glucuronidase epitope, a green fluorescent protein epitope, and a luciferase epitope.

6. A recombinant cell comprising the isolated nucleic acid of claim 1.

7. The cell of claim 6, wherein said cell is selected from the group consisting of a prokaryotic cell and a eukaryotic cell.

8. A vector encoding at least one PCS variant as claimed in claim 1.

9. A transgenic plant stably transformed with an isolated nucleic acid encoding a variant PCS as claimed in claim 8.

10. A method of generating a transgenic heavy metal resistant plant comprising introducing into the cells of the plant an isolated nucleic acid of claim 1, encoding said variant PCS, thereby generating a transgenic heavy metal resistant plant.

11. A method of decreasing the level of a heavy metal in a harvestable portion of a plant, said method comprising expressing the nucleic acid of claim 1 encoding said variant PCS in a non-harvestable portion of a plant, thereby decreasing the level of heavy metal in the harvestable portion of the plant.

12. A method of removing a heavy metal from groundwater, said method comprising growing in said groundwater the transgenic of claim 9, and harvesting said plant from said groundwater, thereby removing said heavy metal from said groundwater.

13. Transgenic cells, seeds or progeny of the stably transformed plant of claim 9, each of which comprise the isolated nucleic acid encoding said variant PCS.

14. A transgenic plant comprising the isolated nucleic acid of claim 2.

15. A transgenic plant comprising the isolated nucleic acid of claim 3.

\* \* \* \* \*